United States Patent
Bender et al.

(10) Patent No.: US 11,331,622 B2
(45) Date of Patent: *May 17, 2022

(54) AIR IONIZATION SYSTEMS AND COMPONENTS

(71) Applicant: IONaer International Arizona, LLC, Glendale, AZ (US)

(72) Inventors: Timothy M. Bender, Scottsdale, AZ (US); Perry Pauley, Glendale, AZ (US); Brian K. Roper, Phoenix, AZ (US); Todd K. Roper, Glendale, AZ (US)

(73) Assignee: IONaer International Arizona, LLC, Glendale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/510,803

(22) Filed: Jul. 12, 2019

(65) Prior Publication Data
US 2020/0009503 A1    Jan. 9, 2020

Related U.S. Application Data

(63) Continuation of application No. 15/622,027, filed on Jun. 13, 2017, now Pat. No. 10,350,541, which is a
(Continued)

(51) Int. Cl.
*B01D 53/32* (2006.01)
*A61L 9/22* (2006.01)
(Continued)

(52) U.S. Cl.
CPC .............. *B01D 53/32* (2013.01); *A61L 9/00* (2013.01); *A61L 9/22* (2013.01); *B01D 46/0027* (2013.01);
(Continued)

(58) Field of Classification Search
CPC ........ A61L 9/22; B01D 53/32; B01D 46/0027
See application file for complete search history.

(56) References Cited

U.S. PATENT DOCUMENTS 6,791,815 B1    9/2004  Graham
8,747,754 B2    6/2014  Abate
(Continued)

OTHER PUBLICATIONS

Non-Final Office Action dated Jun. 30, 2017 in corresponding U.S. Appl. No. 15/156,755, filed May 17, 2016; total 21 pages.
(Continued)

*Primary Examiner* — Kevin Joyner
(74) *Attorney, Agent, or Firm* — Snell & Wilmer L.L.P.

(57) ABSTRACT

Ionization systems and methods include moving air into contact with one or more ion generators and then past an ozone removal assembly to remove at least some ozone from the air. The air may be moved by a fan and may be filtered before contacting the one or more ion generators. The amount of one or more of the following of the air may be measured: the amount of ions, particulates, temperature, humidity, and other relevant factors. The ionization amount may be adjusted based on one or more of the measured amounts. The one or more ion generators and ozone removal assembly may be constructed as part of a single unit so they can be removed and replaced easily.

34 Claims, 28 Drawing Sheets

US 11,331,622 B2
Page 2

Related U.S. Application Data continuation-in-part of application No. 15/156,735, filed on May 17, 2016, now Pat. No. 9,907,874, and a continuation-in-part of application No. 15/156,771, filed on May 17, 2016, now Pat. No. 9,908,082, and a continuation-in-part of application No. 15/156,755, filed on May 17, 2016, now Pat. No. 9,908,081.

(51) Int. Cl.
| | | |
|---|---|---|
| *B01D 46/00* | (2022.01) | |
| *B01D 53/86* | (2006.01) | |
| *B01D 53/30* | (2006.01) | |
| *A61L 9/00* | (2006.01) | |
| *H01T 23/00* | (2006.01) | |
| *F24F 8/192* | (2021.01) | |
| *B01D 53/88* | (2006.01) | |
| *F24F 8/30* | (2021.01) | |
| *F24F 8/98* | (2021.01) | |

(52) U.S. Cl.
CPC ..... *B01D 46/0028* (2013.01); *B01D 46/0038* (2013.01); *B01D 53/30* (2013.01); *B01D 53/323* (2013.01); *B01D 53/8675* (2013.01); *F24F 8/192* (2021.01); *H01T 23/00* (2013.01); *A61L 2209/11* (2013.01); *A61L 2209/13* (2013.01); *A61L 2209/14* (2013.01); *B01D 53/88* (2013.01); *B01D 2255/2073* (2013.01); *B01D 2255/20761* (2013.01); *B01D 2257/106* (2013.01); *B01D 2257/90* (2013.01); *B01D 2258/06* (2013.01); *B01D 2259/4508* (2013.01); *B01D 2259/80* (2013.01); *B01D 2259/818* (2013.01); *F24F 8/30* (2021.01); *F24F 8/98* (2021.01)

(56) References Cited

U.S. PATENT DOCUMENTS

| 9,907,874 | B2 | 3/2018 | Bender et al. | |
|---|---|---|---|---|
| 9,908,081 | B2 | 3/2018 | Bender et al. | |
| 9,908,082 | B2 | 3/2018 | Bender et al. | |
| 2001/0031234 | A1 | 10/2001 | Christodoulatos et al. | |
| 2003/0106788 | A1 | 6/2003 | Babko-Malyi | |
| 2004/0007000 | A1 | 1/2004 | Takeda et al. | |
| 2004/0247497 | A1 | 12/2004 | Yuen | |
| 2007/0098614 | A1* | 5/2007 | Iida | B01J 19/087 423/245.3 |
| 2007/0212273 | A1 | 9/2007 | Edwards | |
| 2007/0253860 | A1 | 11/2007 | Schroder | |
| 2008/0035472 | A1* | 2/2008 | Lepage | A61L 9/22 204/229.8 |
| 2008/0063577 | A1* | 3/2008 | Crowe | A61L 2/14 422/186.04 |
| 2008/0317802 | A1 | 12/2008 | Lee et al. | |
| 2009/0202397 | A1 | 8/2009 | Parker et al. | |
| 2010/0089240 | A1* | 4/2010 | Krichtafovitch | B03C 3/368 96/32 |
| 2014/0198426 | A1* | 7/2014 | Abate | F24F 3/166 361/231 |
| 2015/0017059 | A1* | 1/2015 | Arlemark | A61L 2/10 422/3 |
| 2015/0076082 | A1 | 3/2015 | Loucaides | |
| 2016/0067645 | A1* | 3/2016 | Mutha | B01D 46/0086 340/657 |
| 2016/0263263 | A1 | 9/2016 | Robert | |
| 2017/0056543 | A1 | 3/2017 | Mole | |
| 2017/0189846 | A1 | 7/2017 | Cho et al. | |
| 2017/0333587 | A1 | 11/2017 | Bender et al. | |
| 2017/0333837 | A1 | 11/2017 | Bender et al. | |
| 2017/0333838 | A1 | 11/2017 | Bender et al. | |
| 2017/0348636 | A1 | 12/2017 | Bender et al. | |
| 2018/0036677 | A1 | 2/2018 | Bender et al. | |
| 2018/0193508 | A1 | 7/2018 | Bender et al. | |
| 2018/0193509 | A1 | 7/2018 | Bender et al. | |
| 2018/0193794 | A1 | 7/2018 | Bender et al. | |

OTHER PUBLICATIONS

Notice of Allowance dated Dec. 7, 2017 in corresponding U.S. Appl. No. 15/156,755, filed May 17, 2016; total 9 pages.
Non-Final Office Action dated Jul. 24, 2017 in corresponding U.S. Appl. No. 15/156,771, filed May 17, 2016; total 15 pages.
Notice of Allowance dated Dec. 7, 2017 in corresponding U.S. Appl. No. 15/156,771, filed May 17, 2016; total 10 pages.
Non-Final Office Action dated Jun. 30, 2017 in corresponding U.S. Appl. No. 15/156,735, filed May 17, 2016; total 13 pages.
Notice of Allowance dated Dec. 20, 2017 in corresponding U.S. Appl. No. 15/156,735, filed May 17, 2016; total 13 pages.
Non-Final Office Action dated Nov. 28, 2018 in corresponding U.S. Appl. No. 15/622,027, filed Jun. 13, 2017; total 24 pages.
Notice of Allowance dated Apr. 5, 2019 in corresponding U.S. Appl. No. 15/622,027, filed Jun. 13, 2017; total 9 pages.
Non-Final Office Action dated Nov. 6, 2020 in corresponding U.S. Appl. No. 16/510,785, filed Jul. 12, 2019; total 16 pages.
Final Office Action dated May 18, 2021 in corresponding U.S. Appl. No. 16/510,785, filed Jul. 12, 2019; total 18 pages.
Non-Final Office Action dated Nov. 30, 2018 in corresponding U.S. Appl. No. 15/914,682, filed Mar. 7, 2018; total 26 pages.
Notice of Allowance dated Jun. 12, 2019 in corresponding U.S. Appl. No. 15/914,682, filed Mar. 7, 2018; total 9 pages.
Non-Final Office Action dated Dec. 3, 2018 in corresponding U.S. Appl. No. 15/913,733, filed Mar. 6, 2018; total 22 pages.
Notice of Allowance dated Jun. 12, 2019 in corresponding U.S. Appl. No. 15/913,733, filed Mar. 6, 2018; total 9 pages.
Non-Final Office Action dated Nov. 28, 2018 in corresponding U.S. Appl. No. 15/622,025, filed Jun. 13, 2017; total 19 pages.
Notice of Allowance dated Jul. 17, 2019 in corresponding U.S. Appl. No. 15/622,025, filed Jun. 13, 2017; total 9 pages.

* cited by examiner

AIR IONIZATION SYSTEMS AND COMPONENTS

CROSS REFERENCE TO RELATED APPLICATIONS

This application is a continuation of U.S. patent application Ser. No. 15/622,027, filed on Jun. 13, 2017 and entitled "AIR IONIZATION SYSTEMS AND COMPONENTS", which is a Continuation-in-Part of and claims priority to U.S. patent application Ser. No. 15/156,755 filed on May 17, 2016, now U.S. Pat. No. 9,908,081 entitled "AIR IONIZATION METHODS" and U.S. patent application Ser. No. 15/156,735, filed on May 17, 2016, now U.S. Pat. No. 9,907,874 entitled "AIR IONIZATION SYSTEMS AND METHODS" and U.S. patent application Ser. No. 15/156,771, filed on May 17, 2016, now U.S. Pat. No. 9,908,082 entitled "AIR IONIZATION SYSTEM". The disclosures of the aforementioned applications are incorporated herein by reference in their entirety.

TECHNICAL FIELD

The present disclosure relates to air cleaning, and in particular to the removal of particulates in air by utilizing ionization.

BACKGROUND

Prior approaches to air filtration and/or ionization suffer from various drawbacks. For example, certain air ionization systems, in order to avoid releasing an unacceptable level of ozone, generate ionization levels that are insufficient to fully clean and/or sanitize a particular air stream. Moreover, some air ionization systems have suffered from a lack of configurability and/or intelligent control. Yet other air ionization systems have been complex, expensive, and/or lacking in modular configuration and/or serviceability. These and other drawbacks of prior approaches may remedied by principles of the present disclosure.

SUMMARY OF THE INVENTION

Disclosed are air ionization devices, systems, and methods that include an ozone dampening catalyst and an air ionization tube. The ozone dampening catalyst removes at least some of the ozone created by ionizing molecules in the air. In one embodiment, rather than the air passing by the ionization tube and being ionized in a known manner, air is drawn into an ionization module, and may pass through a filter that may be part of the module. The air then moves outward into a space between the ionization tube and the ozone dampening catalyst, and it can be pushed through the space by a fan. The air is ionized by the ionization tube, which usually creates some ozone. The ozone is partially or totally removed by the ozone absorption tube as the air passes through it. Alternatively, the ozone dampening catalyst may be in a filter located at a position such that air passes the ionization tube and is ionized, and then passes through the ozone dampening catalyst. The ozone dampening catalyst may be in a filter (which means any suitable structure to permit air flow through and be exposed to the catalyst) above, below or alongside of the ionization tube.

An air ionization unit is preferably an integral, one-piece unit, so it can be removed from a surface to which it is mounted. That way it can be replaced as a single unit without having to disassemble it. In one preferred embodiment, the air ionization unit has a support plate that mounts directly or indirectly to the outside surface of an air passageway or other space (collectively, "duct") that includes air to be cleaned. The support plate is connected to a surface defining a duct by fasteners that pass through the support plate and through the material of the surface duct. The air ionization tube and ozone dampening catalyst preferably are attached to and extend outward from the support plate and into the air duct. The fasteners holding the support plate on the exterior surface of the air duct can be removed to remove the support plate, air ionization tube and/or replace the entire air ionization unit.

The invention may also include a controller that (1) measures the amount of particulate in the air, (2) measures the amount of negative and/or positive ions in the air, (3) measures the amount of ozone in the air, (4) measures the amount of carbon monoxide in the air, (5) measures the air temperature and humidity, (6) measures the air flow rate through a filter, (7) adjusts the amount of ions being released into the air based on one or more measured parameters, (8) displays one or more of the measured parameters, and/or (9) provides an alert when a parameter is at a certain level.

Also disclosed are alternative ionization tubes and tube configurations that can be used to reduce the cross-sectional area in which the tube(s) are positioned and/or that provide greater ionization in the same cross-sectional area as known ionization tubes.

DETAILED DESCRIPTION

Figure 1:
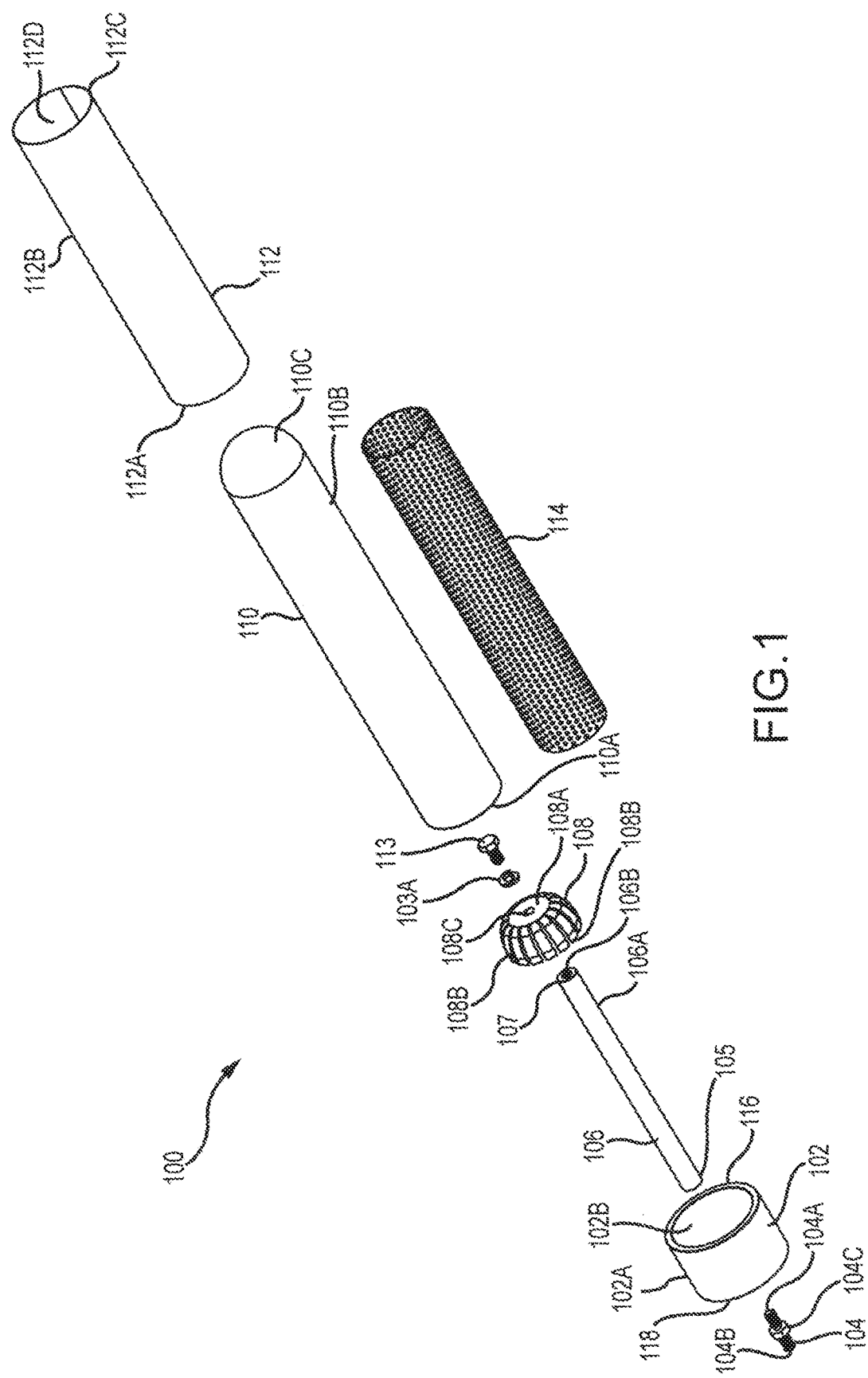
FIG. 1 is an exploded view of an air ionization unit in accordance with embodiments of the invention.
Figure 2:
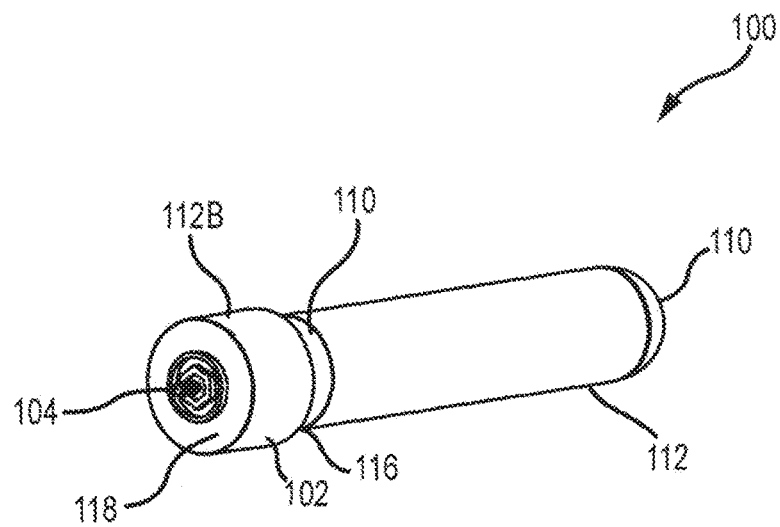
FIG. 2 is an assembled, perspective side view of the air ionization unit of FIG. 1.
Figure 3:
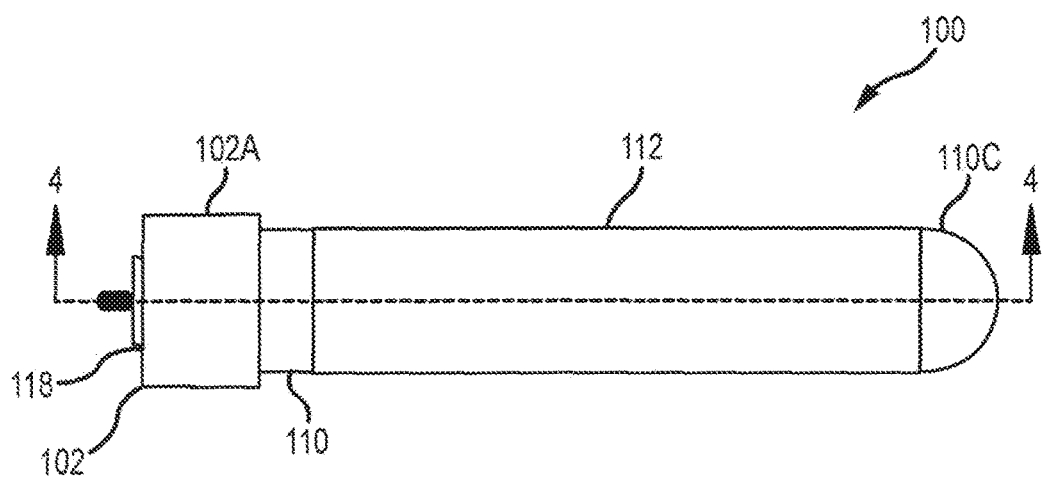
FIG. 3 is an assembled side view of the air ionization unit of FIG. 1.
Figure 4:
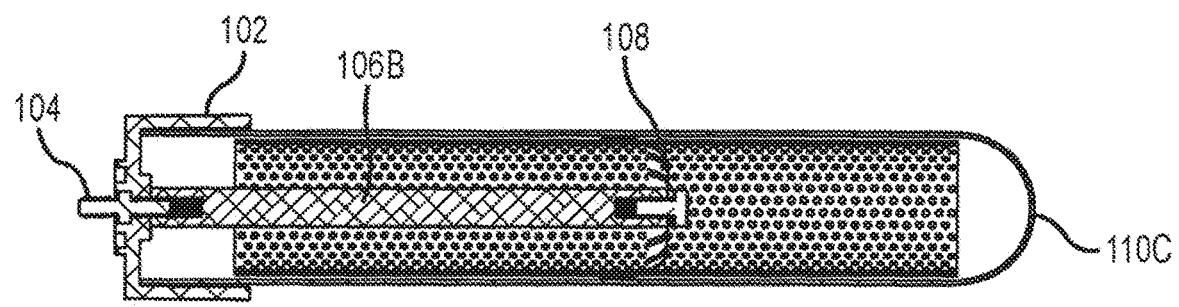
FIG. 4 is a cross-sectional, side view of the air ionization unit of FIG. 3 taken along lines A-A.
Figures 5, 6:
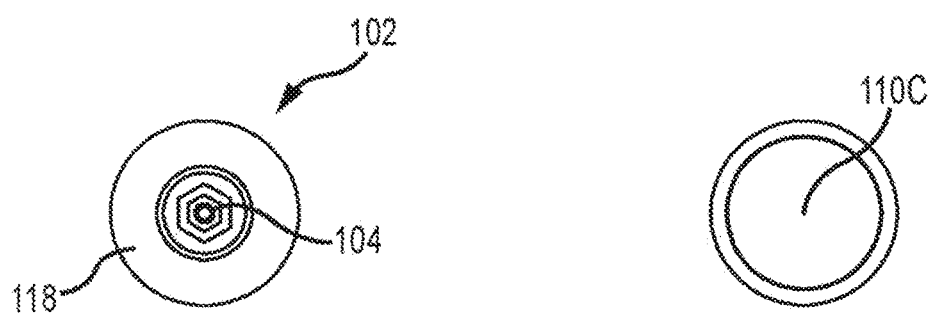
FIG. 5 is an end view of the air ionization unit of FIG. 3.
FIG. 6 is the opposite end view of the air ionization unit of FIG. 3.

The following description is of various exemplary embodiments only, and is not intended to limit the scope of the present disclosure in any way. As will become apparent, various changes may be made in the function and arrangement of the elements described in these embodiments without departing from the scope of the appended claims.

It should be noted that many alternative or additional functional relationships or physical connections may be present in a practical ionization system or related methods.

Turning now to FIGS. 1 through 6, a module 100 for ionizing air is shown. Module 100 as shown preferably has an end cap or "base" 102, an adapter 104, a coupler 106, an ion dispenser 108, a tube 110, an outer electrode 112, and an inner electrode 114. Base 102 is preferably comprised of any suitable plastic, for example injection-molded ABS (but preferably not ABS-PC), although any suitable material may be used. The purpose of base 102 is to receive coupler 106, ion dispenser 108, and tube 110.

Coupler 106 has a first end 105, a second end 107, an outer surface 106A, and a passageway 106B extending therethrough. In some embodiments, coupler 106 comprises a hollow aluminum rod. Moreover, coupler 106 may comprise a solid bar with an internal thread on each end. Coupler 106 may be configured to conduct electricity.

Adapter 104 as shown is a threaded shaft that bases through an opening (not shown in these Figures) of second end 118 of base 102 and is threadingly received in a passageway 106B at the first end 105 of coupler 106. The opening in second end 118 may also be threaded so as to threadingly receive adapter 104. In the preferred embodiment shown, adapter 104 is a threaded shaft with a first end 104A and a second end 104B. A nut 104C is threadingly received on the threaded shaft end 105 of coupler 106, which is aligned with the opening on the inside of second end 118. First end 104A passes through the opening and is threadingly received in passageway 106B of coupler 106 to retain coupler 106 against second end 118. In some exemplary embodiments, adapter 104 may comprise a solid stainless steel adapter with threaded ends and a central integral hex feature to facilitate rotation thereof.

An ion dispenser (also called an "umbrella shaped conductor") 108 is attached to second end 107 of coupler 106. In various exemplary embodiments, ion dispenser 108 may be configured with an umbrella-like shape. However, ion dispenser 108 may be configured with any suitable shape, as desired. Ion dispenser 108 operates to dispense electricity into inner electrode 114. Ion dispenser 108 as shown in this preferred embodiment is comprised of stainless steel (for example, stainless steel having a thickness of between about 0.006 inches and about 0.015 inches), has a top 108A for attachment to coupler 106, and a plurality of downward extending fingers 108B. In this preferred embodiment, ion dispenser 108 is attached to coupler 106 by aligning an opening in top 108A with passageway 106B at end 107 of coupler 106. Then fastener 113, which as shown is a bolt, is passed through opening 108C and threaded into passageway 106B. A lock washer 113A may be positioned between top 108A and the head of fastener 113.

Inner electrode 114 typically comprises a rolled perforated aluminum sheet, but may comprise any suitable material or combination of materials configured to act as a first electrode for purposes of ionization.

Outer electrode 112 typically comprises a tubular stainless steel wire mesh, for example a 0.008 in diameter Type 316 stainless steel wire mesh configured with a 20×20 per square inch grid. However, outer electrode 112 may comprise any suitable material or combination of materials configured to act as a second electrode for purposes of ionization.

A tube 110 is preferably glass (for example, comprised of borosilicate) and retains coupler 106 and ion dispenser 108. Tube 110 is also operative to insulate inner electrode 114 from outer electrode 112 and thus permit the development of a voltage potential therebetween in order to facilitate ionization. Tube 110 has a first, open end 110A, an outer surface 110B, and a second end 110C. Preferably, after cap 102, coupler 106, and ion dispenser 108 are assembled, inner electrode 114 is placed within tube 110, the first end 110A of tube 110 is positioned over ion dispenser 108 and coupler 106, and is received in cap 102 in a snug to slightly loose fit.

Outer electrode 112, which has a first end 112A, an outer surface 112B, a second end 112C, and an inner passage 112D, is positioned over tube 110. In the preferred embodiment shown, outer electrode 112 does not cover second end 110C of tube 110 or extend to cap 102.

In the preferred embodiment, when module 100 is assembled, coupler 106 and ion dispenser 108 are positioned approximately 50-60% inside the length of tube 110, although any suitable percentage is acceptable. In this manner, electrical current is delivered to the inside of, and approximately the center of, inner electrode 114.

Figure 7:
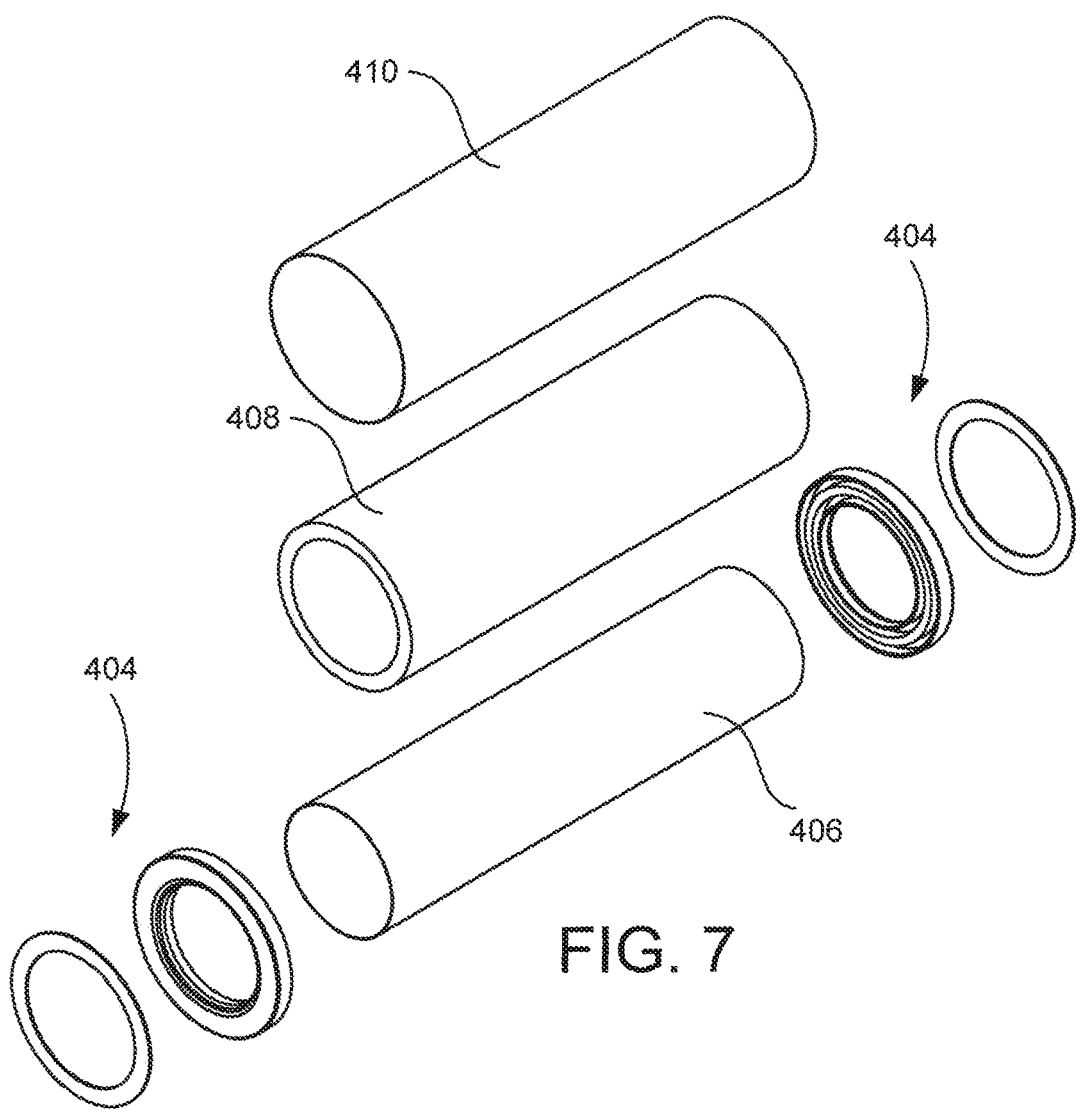
FIG. 7 is an exploded view of an ozone dampening module according to aspects of the invention.
Figure 8:
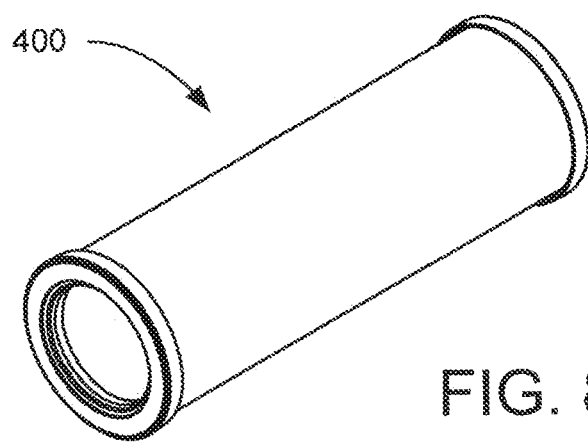
FIG. 8 is a perspective, side view of the assembled ozone dampening module of FIG. 7.
Figure 9:
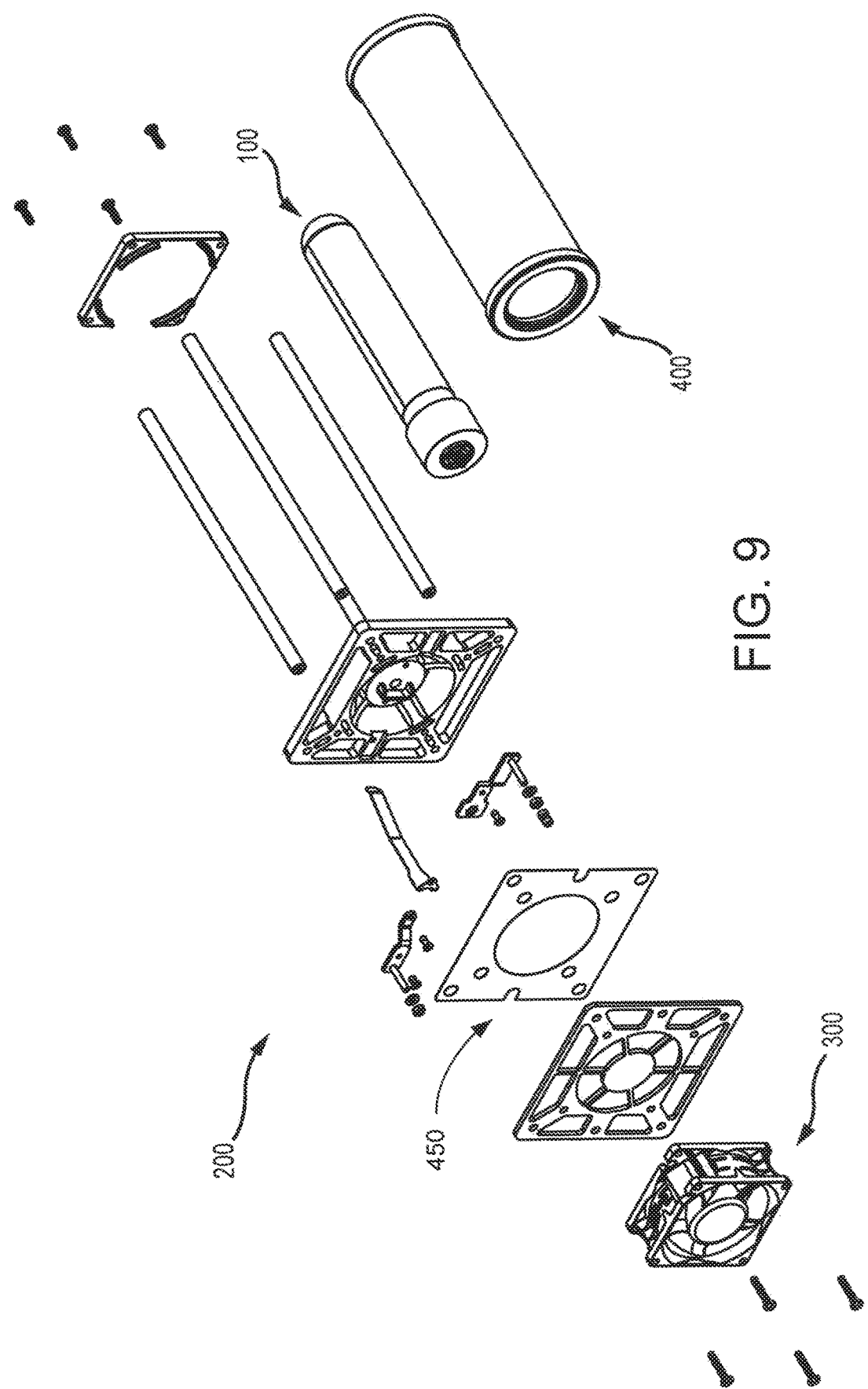
FIG. 9 is an exploded view of an ionization module according to aspects of the invention.
Figure 10:
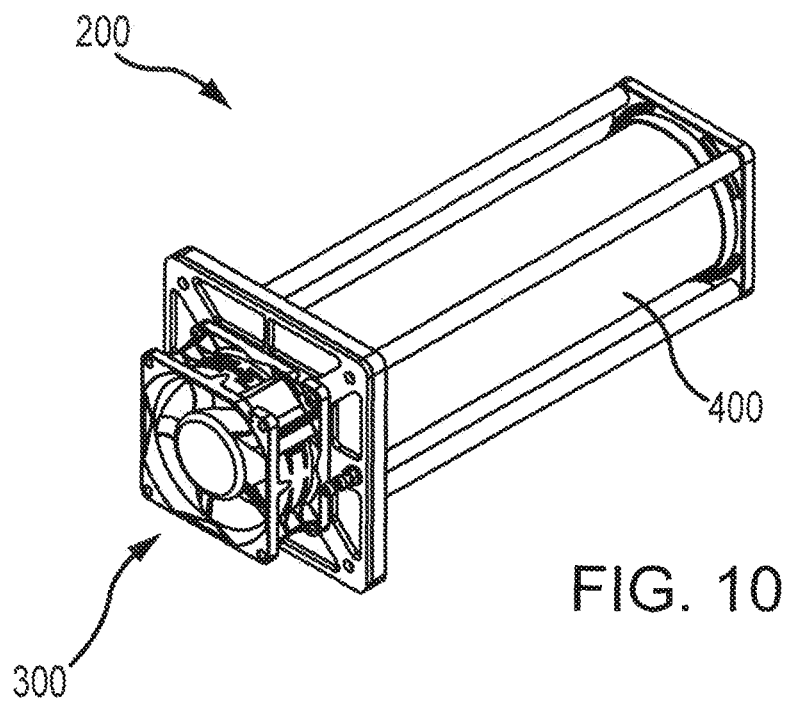
FIG. 10 is an assembled, perspective side view of the ionization module of FIG. 9.
Figure 11:
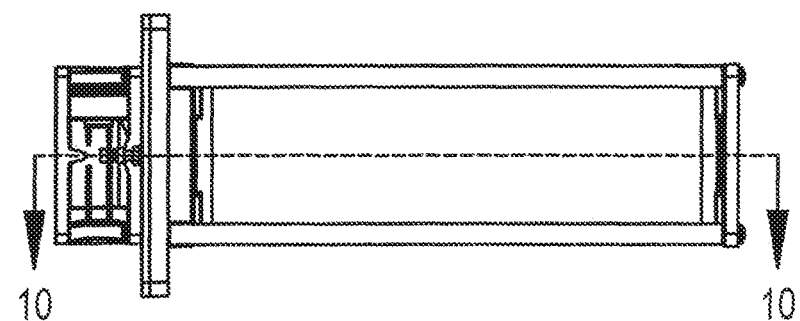
FIG. 11 is an assembled, side view of the ionization module of FIG. 9.
Figure 12:
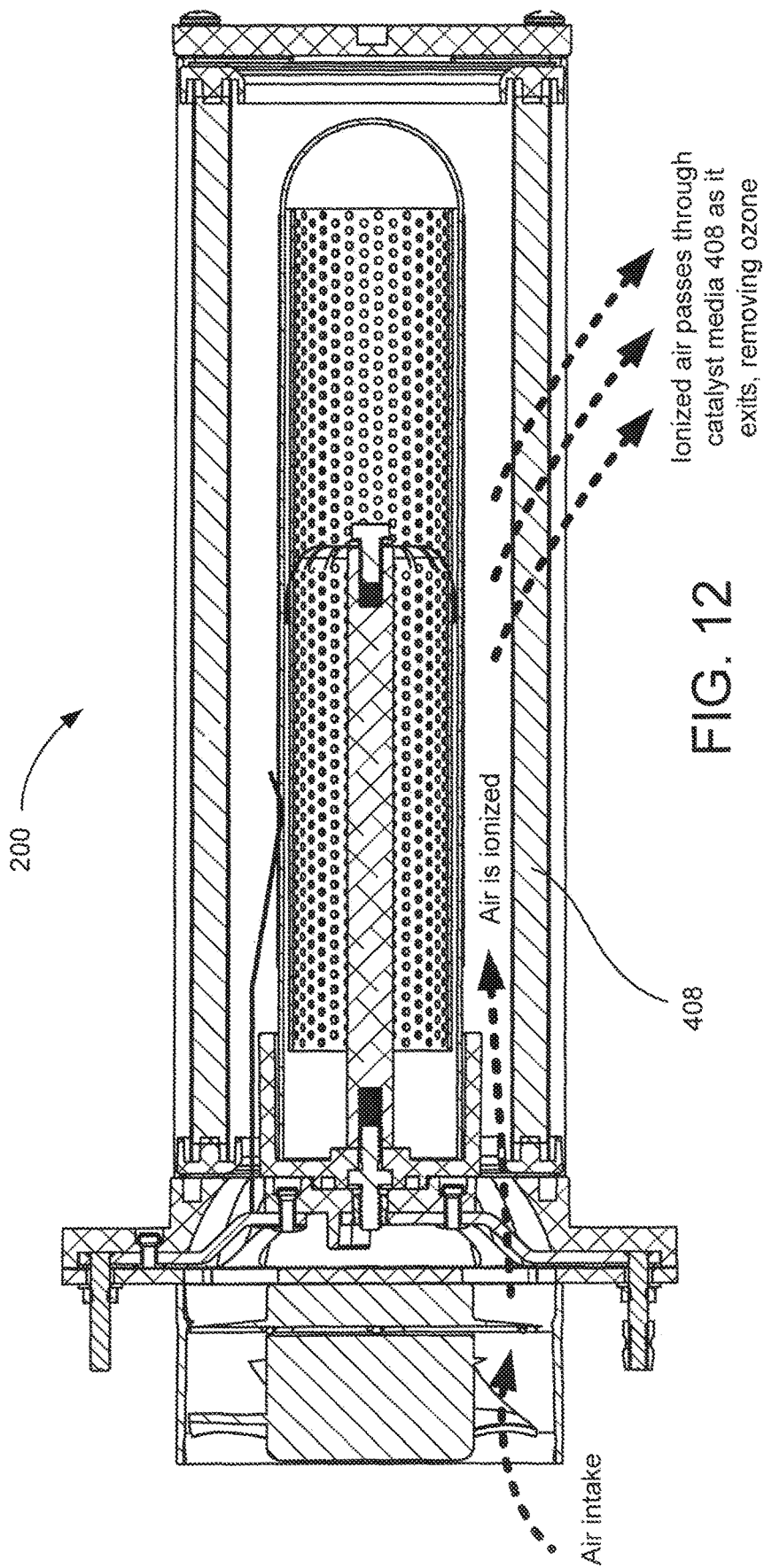
FIG. 12 is a cross-sectional, side view of the ionization module of FIG. 11 taken along lines A-A.
Figure 13:
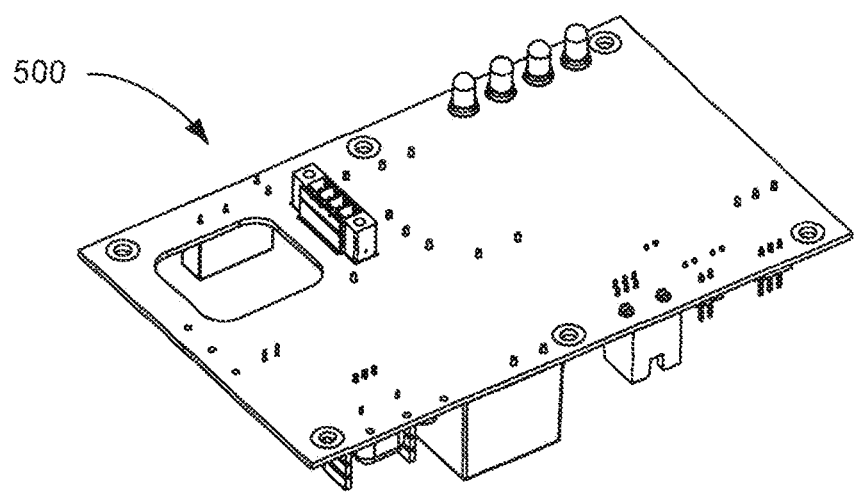
FIG. 13 is a rear, perspective view of a control unit according to aspects of the invention.
Figure 14:
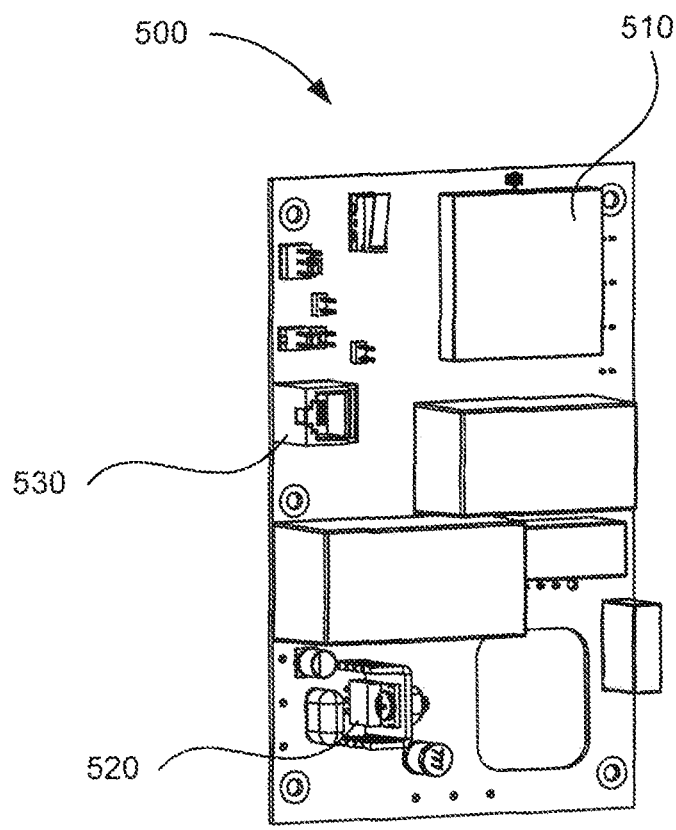
FIG. 14 is a front, perspective view of the control unit of FIG. 13.
Figure 17:
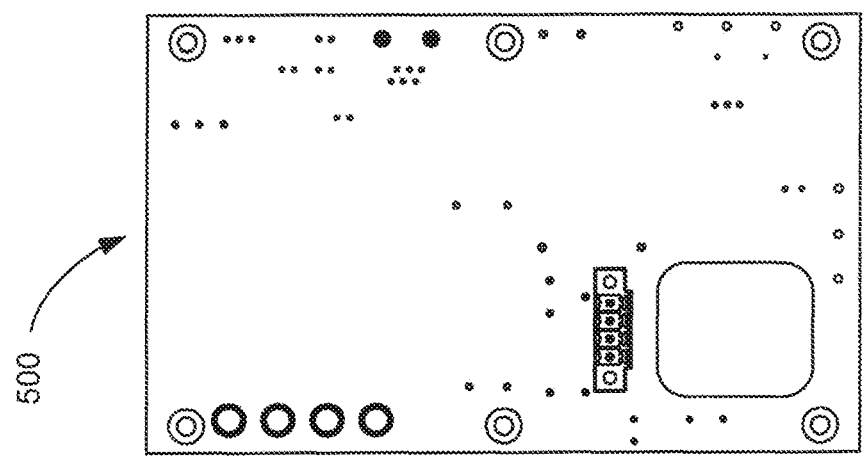
FIG. 17 is a rear view of the control unit of FIG. 13.
Figure 16:
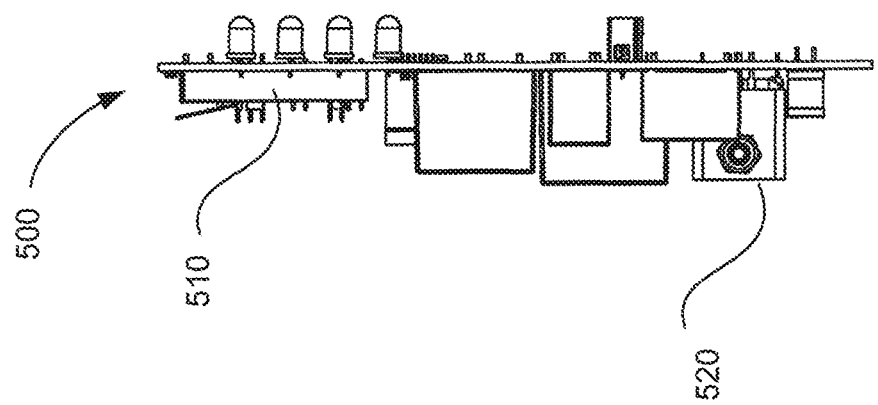
FIG. 16 is a side view of the control unit of FIG. 13.
Figure 15:
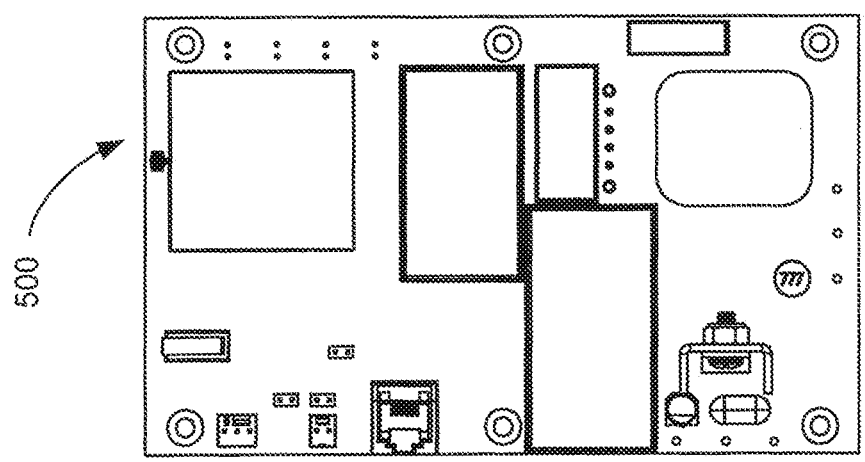
FIG. 15 is a front view of the control unit of FIG. 13.
Figure 18:
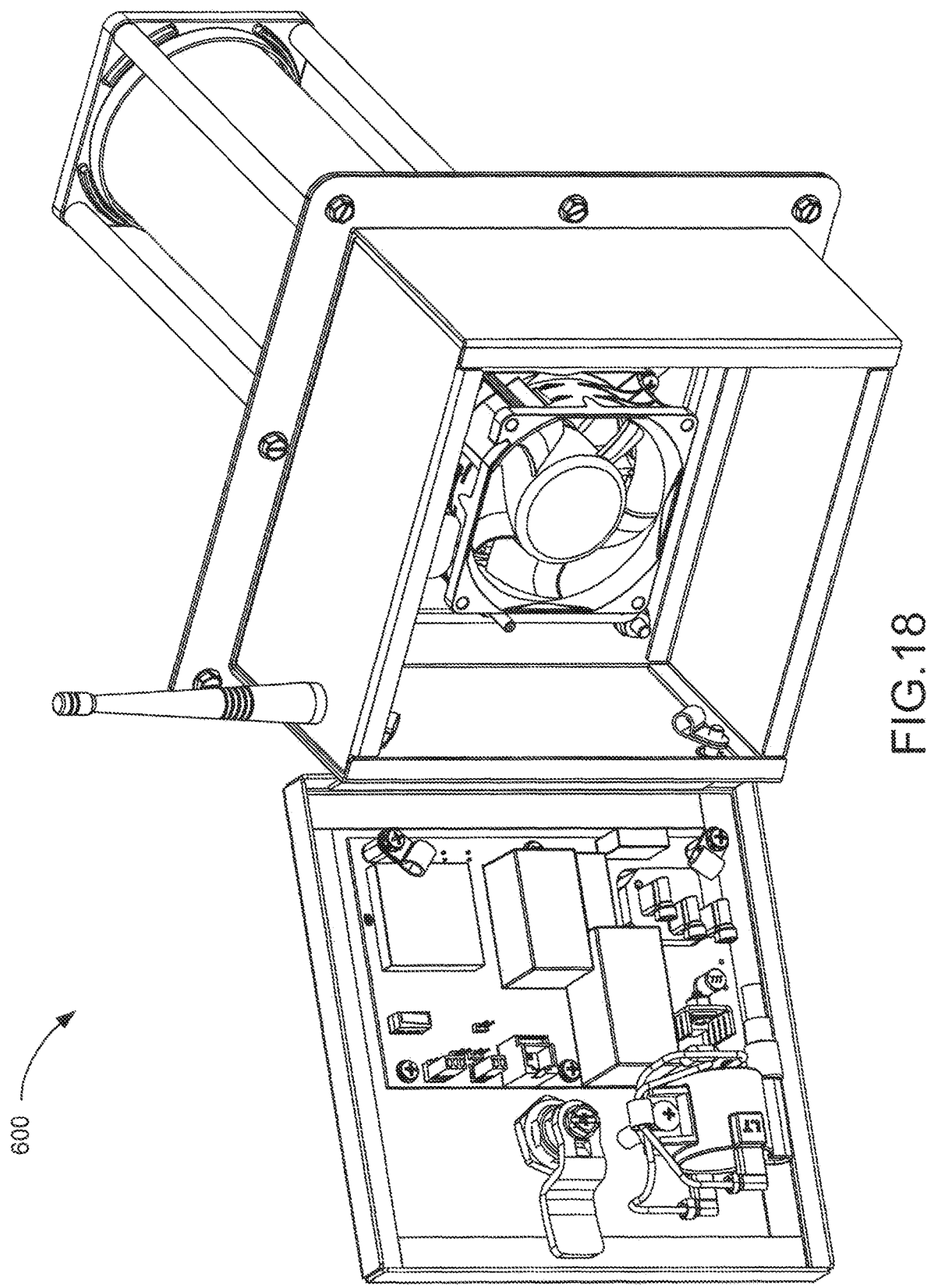
FIG. 18 is a perspective, side view of an ionization system in accordance with aspects of the invention with the housing opened.
Figure 19:
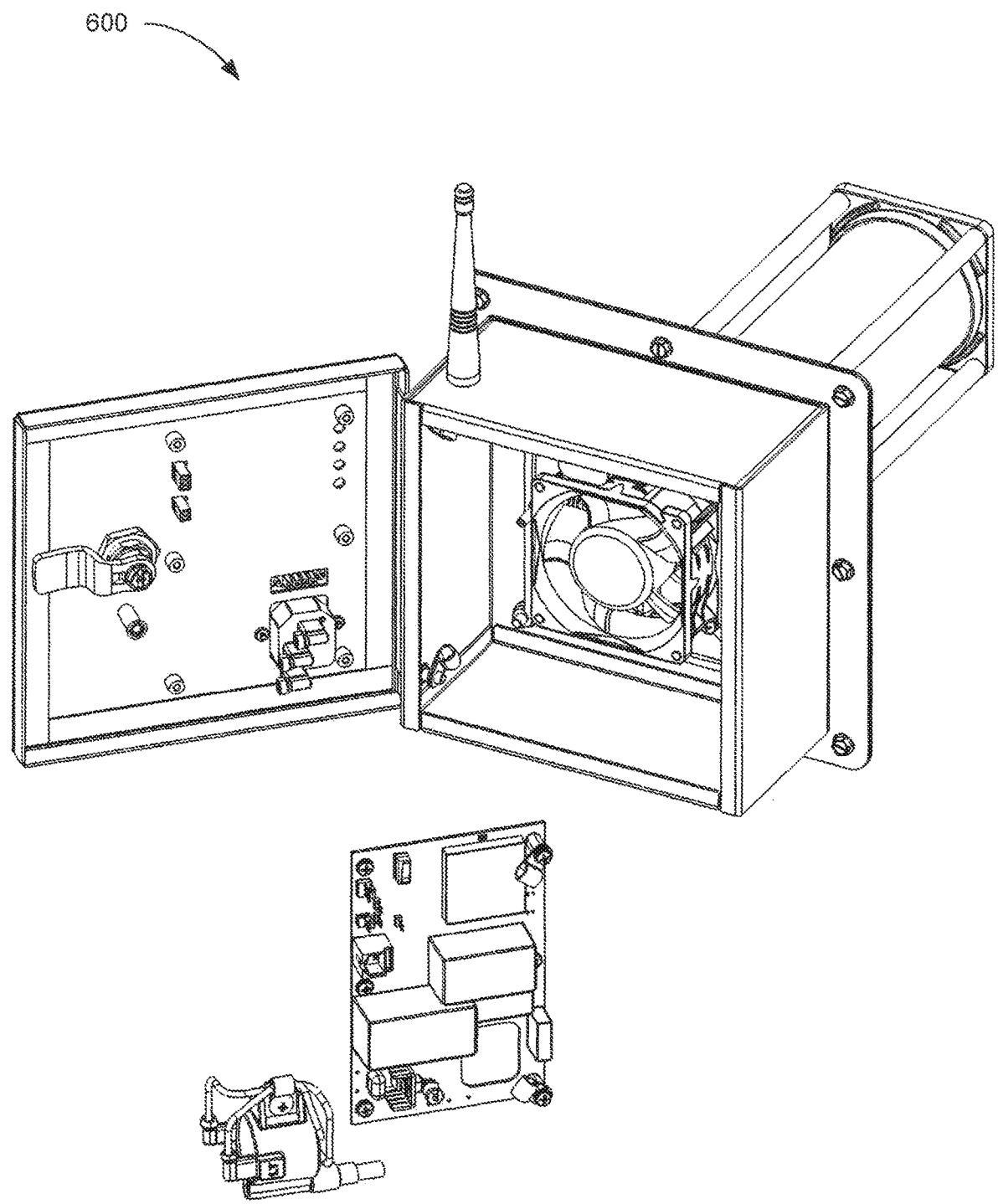
FIG. 19 is a perspective, side view of the ionization system according to FIG. 18 with the control unit and energy converter removed.
Figure 20:
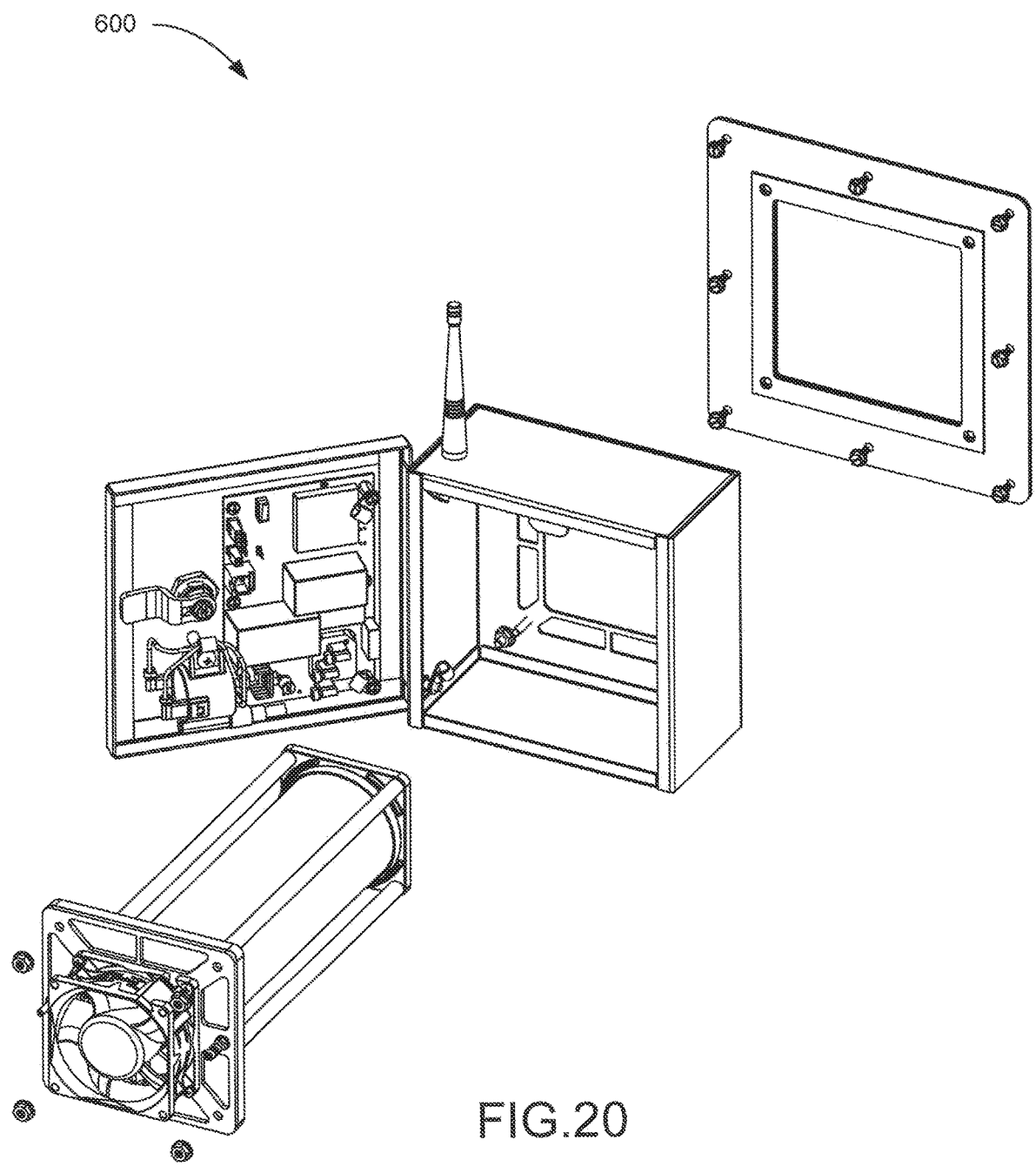
FIG. 20 is a partial exploded view of the ionization system of FIG. 18 showing the ionization module removed from the housing, and the housing removed from a support plate.
Figure 21:
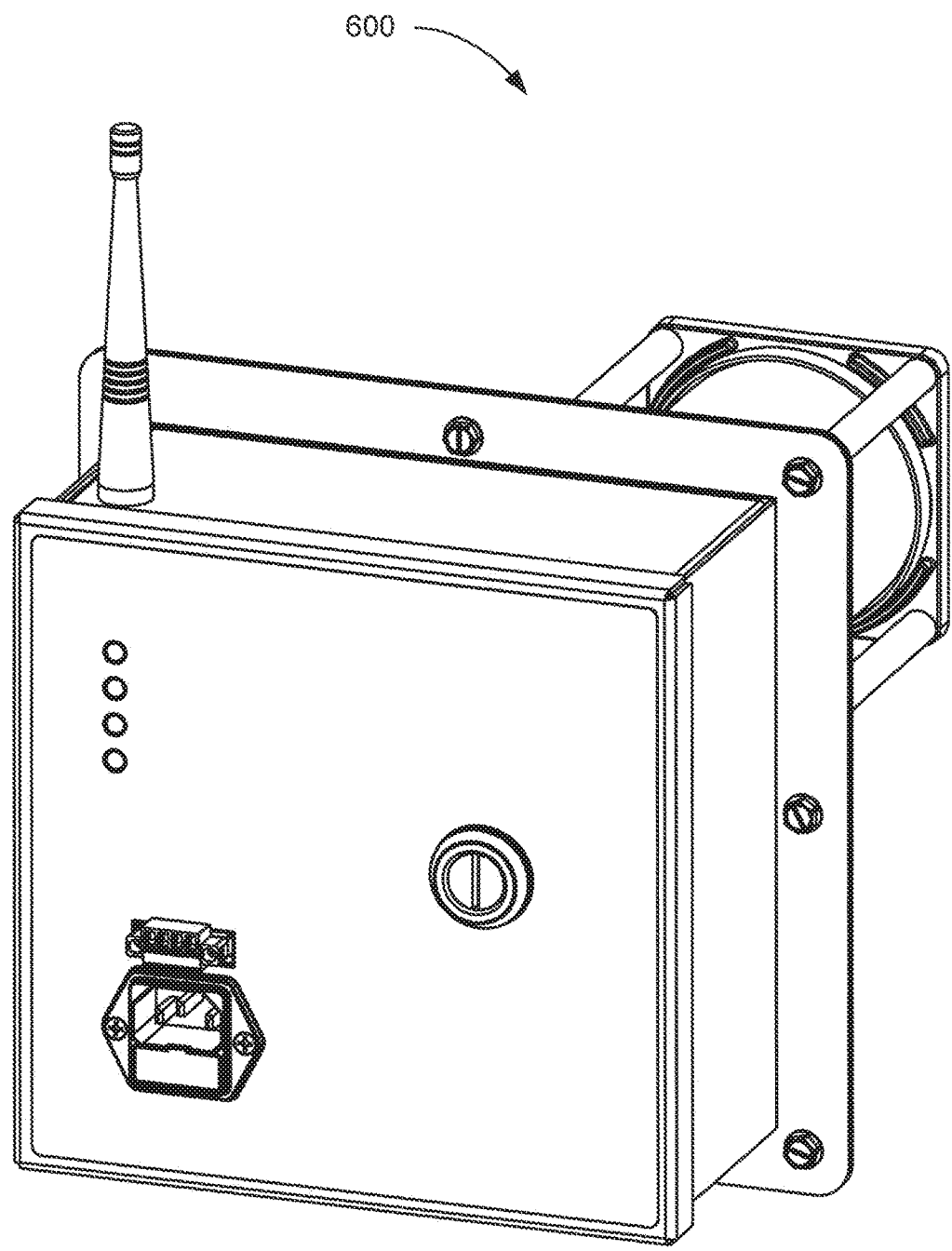
FIG. 21 shows a front, perspective view of an ionization system according to the invention.

With reference now to FIGS. 7 and 8, an ozone removal assembly 400 comprises a tubular inner wall 406, a tubular outer wall 410, and a pair of ends 404. Inner wall 406, outer wall 410, and ends 404 may be coupled together to form a container for a catalyst media 408. In an exemplary embodiment, inner wall 406 and outer wall 410 are coupled to a first end 404 (for example, via RTV silicone). First end 404 is disposed on a surface, and the space between inner wall 406 and outer wall 410 is filled with catalyst media 408. Second end 404 is then coupled to inner wall 406 and outer wall 410, securing catalyst media 408 in the resulting assembly. Inner wall 406 and outer wall 410 are configured to be at least partially permeable to air. For example, inner wall 406 and outer wall 410 may comprise rolled stainless steel mesh screen or the like.

In various exemplary embodiments, catalyst media 408 is configured to convert, neutralize, and/or otherwise remove and/or reduce an undesirable compound in the air, for example ozone. Catalyst media 408 may also be referred to as a "catalyst bed", "reaction bed", "ozone destruction catalyst", and/or the like. Catalyst media 408 may be granulated or otherwise shaped or formed to form part of ozone removal assembly 400. Catalyst media 408 typically comprises manganese dioxide, copper oxide, and/or the like, or combinations of the same. In some embodiments, catalyst media 408 comprises Carulite 200 offered by Cams Corporation (Peru, Ill.). However, any suitable catalyst configured to neutralize and/or remove ozone from an airstream may be utilized.

FIGS. 9 through 12 show an ionization and filter cartridge 200 according to a preferred embodiment of the invention. Cartridge 200 includes previously described module 100. It also generally includes a housing and support structure, a fan assembly (or fan) 300, an ozone removal assembly 400, and an air filter 450. Air filter 450 may comprise polypropylene, natural fibers, and/or the like. Air filter 450 is operative to reduce the amount of dust and other airborne particulates entering ozone removal assembly 400, as accumulation of dust on catalyst media 408 reduces its efficacy.

The support structure of cartridge 200 includes a section for supporting module 100 and ozone removal assembly 400, and a section for supporting fan assembly 300, wherein in the preferred embodiment, when cartridge 200 is fully assembled, it is a single unit that may be removed and replaced when desired.

Turning now to FIGS. 13 through 23, an exemplary ionization and filtration system 600 utilizes module 100 and cartridge 200. System 600 further comprises electronic controls 500. In various exemplary embodiments, electronic controls 500 are configured to control module 100 to generate an ionization level in excess of 66% negative ions; a negative ionization level significantly higher than previous systems. In this manner, module 100 generates a net excess of negative ions, and thus improved air filtration and clearing is achieved. In contrast, prior ionization systems typically generated approximately 50% positive ions and 50% negative ions, thus achieving limited efficacy as many ions quickly recombined and/or neutralized one another and were thus no longer available for air filtration and clearing. In some exemplary embodiments, electronic controls 500 pulse power convertors 520 in a manner suitable to positively bias power convertors 520 with respect to circuit ground; this results in generation of excess negative ions in module 100.

Additionally, electronic controls 500 may further comprise and/or communicate with various inputs (e.g., sensors) which monitor ionization levels, the density of particulates in the air, the ambient humidity, temperature, and/or the like. Based at least in part on the sensor inputs, electronic controls 500 adjust the operation of system 600 to achieve a desired level of filtration, ionization level, and/or the like.

With reference now to FIGS. 13 through 17, electronic controls 500 typically comprise various electronic components, for example: a printed circuit board; RF module 510 for wireless communication via a suitable wireless protocol or protocols (for example, IEEE 802.11 ("WiFi"), IEEE 802.15.4 ("ZigBee"), Bluetooth, GSM, and/or the like); power convertor(s) 520 for creating, modulating, transforming, and/or converting AC and/or DC current, for example for use in operating module 100 to produce ions; wired communication and/or input programming port(s) 530; together with various resistors, capacitors, inductors, transistors, diodes, light-emitting diodes, switches, traces, jumpers, fuses, amplifiers, antennas, and so forth as are known in the art. In various exemplary embodiments, electronic controls 500 further comprise a microprocessor and/or microcontroller (for example, an 8-bit or 16-bit microcontroller, such as the PIC16F1503T-I/SL microcontroller offered by MicroChip Corporation of Chandler, Ariz.). The microcontroller is operative for algorithmic (e.g., pre-programmed) operation, as well as responsive (e.g., pursuant to sensor inputs, communications, etc.) operation of system 600.

In one operating mode, electronic controls 500 are configured to operate module 100 at an 80% duty cycle (for example, 4 minutes in an ion generation mode, followed by one minute powered down, followed by 4 minutes in an ion generation mode, and so forth). In another operating mode, electronic controls 500 are configured to operate module 100 at a 100% duty cycle (always on). However, any suitable duty cycle may be utilized.

In various exemplary embodiments, electronic controls 500 are configured to generate up to 6000 volts at frequencies between 1 kHz and 2 kHz for use in ionization. Electronic controls 500 typically draw between about 700 milliamps and about 900 milliamps. Power supplied to module 100 via electronic controls 500 may be digitally managed, for example via a pulse width modulation (PWM) technique utilizing a fixed voltage and variable duty cycle. Moreover, operating parameters for electronic controls 500 may be remotely managed.

In various exemplary embodiments, electronic controls 500 employ a "white noise" mode wherein power convertors 520 are turned on and/or off via randomized timing. In this manner, transformer "whine" or "power line hum" may be reduced and/or eliminated, making the resulting system quieter and/or more suitable for indoor use.

In yet another operating mode, electronic controls 500 are configured to operate system 600 in an "ozone depletion mode" whereby module 100 is powered down and does not create ionization, but air is still passed through catalyst media 408, for example responsive to operation of fan assembly 100 (and/or as a result of ambient airstream movement, for example in an HVAC duct). In this manner, system 600 is operative to remove ozone from the ambient air.

In various exemplary embodiments, electronic controls 500 monitor the performance of module 100 and/or ozone removal assembly 400, and may signal when a component of system 600 needs replacing (for example, due to deterioration of ionization components in module 100, due to dust accumulation on catalyst media 408 in module 400, and/or the like).

Electronic controls 500 are configured to monitor and control various operational characteristics of system 600, for example for safety. In various embodiments, electronic controls 500 monitor fan 300 speed and current draw, as well as module 100 voltage and current draw. System 600 may be shut down and/or restarted if an anomaly is detected. Additionally, electronic controls 500 may monitor status and error conditions, turn an ozone depletion mode on or off, monitor temperature limits for operation, and/or adjust a duty cycle associated with operation of module 100.

With reference now to FIGS. 18 through 21, system 600 may be configured to be installed in a ventilation duct, for example an existing HVAC duct of a building. System 600 may be installed in connection with a new build, or as a retrofit.

While various exemplary embodiments of system 600 may be discussed in the context of a residential HVAC installation, it will be appreciated that embodiments of the invention may be deployed in a wide variety of form factors, installation locations, and uses. For example, system 600 may be configured as: a desktop unit for placing on an office desk; a freestanding unit (for example, similar in form factor to a tower-style fan); a unit for installation in a vehicle such as an automobile, bus, or airplane; or a high-volume unit for use in connection with a hospital, school, food processing plant, restaurant, and/or the like. In particular, system 600 may desirably be utilized to sanitize and deodorize air that is exposed to or contains strong-smelling organic contaminants, reducing and/or eliminating undesirable odors.

Figure 22:
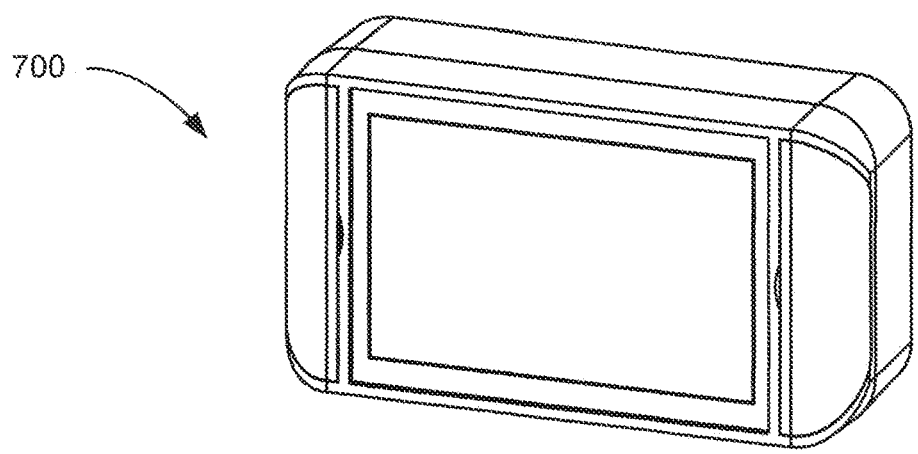
FIG. 22 shows a display that may be used in accordance with aspects of the invention.

In some embodiments, with reference to FIG. 22 system 600 may further comprise a control panel 700. Control panel 700 comprises a display and various inputs, buttons, and the like. Control panel 700 is in wired and/or wireless communication with control electronics 500. Via control panel 700, a user may view statistics regarding operation of system 600, give commands to system 600, view error messages or other system 600 communications, and the like.

Figure 23:
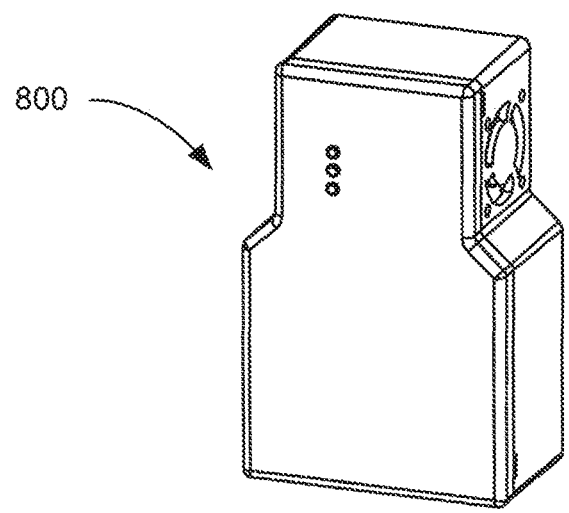
FIG. 23 shows a sensor that may be used in accordance with aspects of the invention.

In various embodiments, with reference to FIG. 23 system 600 may further comprise one or more remote sensors 800. Remote sensor 800 is in wired and/or wireless communication with control electronics 500. Remote sensor 800 comprises various sensors, for example a temperature sensor, particulate sensor, ozone sensor, carbon monoxide sensor, humidity sensor, and/or the like. Responsive to information received from remote sensor 800, control electronics 500 may modify operation of system 600, for example turning module 100 on or off, turning fan 300 on or off, and/or the like. For example, when remote sensor 800 reports ambient ozone above a target threshold, control electronics 500 may operate system 600 in an ozone depletion mode for a period of time until ambient ozone is below a target threshold. Likewise, when remote sensor 800 reports that particulates are above a target threshold, control electronics 500 may increase the duty cycle of module 100 in order to generate increased ionization and thus increase the rate of particulate removal. Remote sensor 800 may be battery powered, or may be configured to be plugged into a power outlet. Multiple sensors 800 may be utilized to provide information regarding an operational environment to control electronics 500.

In various exemplary embodiments, operating parameters for system 600 may be monitored and changed remotely, for example via wireless communication. Changes for system 600 may be supplied via a connected software application operable on a tablet or smartphone, via control panel 700, via a universal serial bus connection to control electronics 500, and/or the like.

Alternate Module Configurations for Ionizing Air

Any of the alternative module configurations described herein may be used in systems or devices as previously described, or as described below. The alternative module configurations function in the same manner and have the same components as module 100, but they have different shapes, and/or different configurations, which makes them better suited for certain uses.

Figure 24:
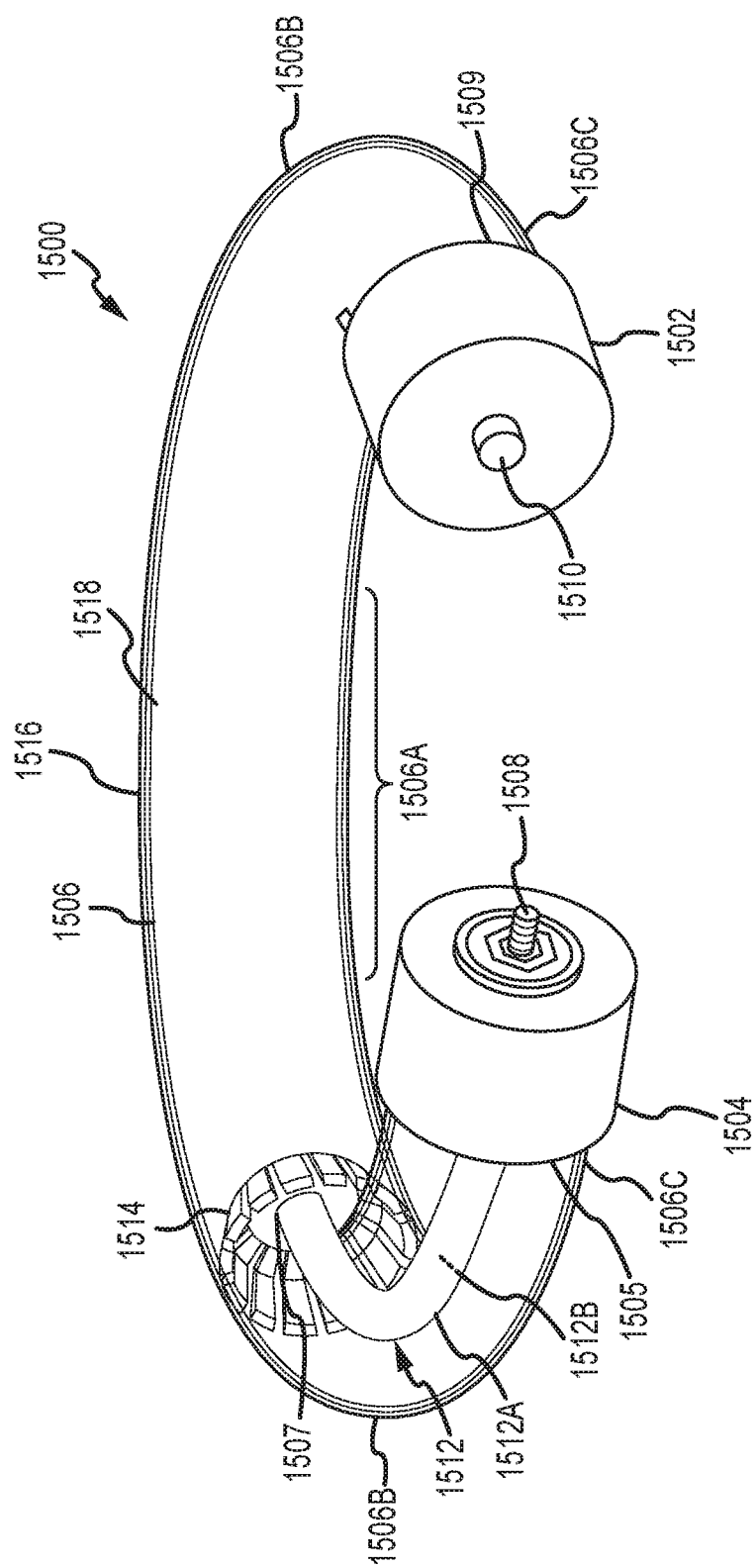
FIG. 24 shows a helical ionization tube that may be used with aspects of the invention.

FIG. 24 shows a curved, or semicircular, module 1500. Module 1500 has the same components as module 100, except that some are shaped, and potentially sized, differently. Module 1500 has two end caps 1502 and 1504. Module 1500 has an adapter 1508 (which is the same as previously described adaptor 104), a curved coupler 1512 (which functions in the same manner as previously-described straight coupler 106), an ion dispenser 1514 (which functions in the same manner and has the same design and sub-structures as previously-described ion dispenser 108), a tube 1506 (which is formed of the same material and functions in the same manner as previously-described tube 110), an outer electrode 1516 and an inner electrode 1518 (which, other than their shape, are positioned, and function, respectively, in the same manner as previously-described outer electrode 112 and inner electrode 114).

End caps 1502, 1504 are preferably comprised of any suitable material, such as injection-molded ABS. Cap 1504 has the same structure as previously-described cap 102, and receives and supports coupler 1512, ion dispenser 1514, and tube 1506.

Coupler 1512 has a first end 1505, a second end 1507, an outer surface 1512A, and a passageway 1512B extending therethrough. In some embodiments, coupler 1512 comprises a hollow aluminum rod. Coupler 1512 may instead be a solid bar (which could comprise aluminum) with an internal threaded bore on each end to attach to other structures. Coupler 1512 may conduct electricity, and preferably does.

Adaptor 1508 as shown is a threaded shaft that passes through an opening (best seen in FIG. 24D) and is threadingly received in a passageway 1521, preferably in the same manner as threaded shaft 104 is attached to module 100.

An ion dispenser 1514 is attached to second end 1507 of coupler 1512. In an exemplary embodiment, ion dispenser 1514 may be configured with an umbrella-like shape, such as the shape of ion dispenser 108. However, ion dispenser 1514 may be configured with any suitable shape, as desired. Ion dispenser 1514 operates to dispense electricity to inner electrode 1518. Ion dispenser 1514 as shown in this preferred embodiment is comprised of stainless steel (for example, stainless steel having a thickness of between about 0.006 inches and about 0.015 inches), and preferably has the same structures and materials as previously-described ion dispenser 108, and is attached to coupler 1512 in the same manner as ion dispenser 108 is attached to coupler 106.

Inner electrode 1518 typically comprises a rolled perforated aluminum sheet, but may comprise any suitable material or combination of materials configured to act as a first electrode for purposes of ionization.

Outer electrode 1516 typically comprises a tubular stainless steel wire mesh, for example a 0.008 in diameter Type 316 stainless steel wire mesh configured with a 20×20 per square inch grid. However, outer electrode 1516 may comprise any suitable material or combination of materials configured to act as a second electrode for purposes of ionization.

A tube 1506 is preferably glass (for example, comprised of borosilicate) and retains coupler 1512, and ion dispenser 1514, and inner electrode 1518. Tube 1506 is also operative to insulate inner electrode 1518 from outer electrode 1516 and thus permit the development of a voltage potential therebetween in order to facilitate ionization. Tube 1506 has a first, open end 1505, a second, open end 1509, and an outer surface. Preferably, after cap 1504, coupler 1512, and ion dispenser 1514 are assembled, inner electrode 1518 is placed within tube 1506, the first end 1505 of tube 1506 is positioned over ion dispenser 1514 and coupler 1512, and is received in cap 1504 in a snug to slightly loose fit.

Outer electrode 1516, which has a first end 1516A, an outer surface 1516B, a second end 1516C, and an inner passage into which tube 1506 is received, is positioned over tube 1506. In the preferred embodiment shown, outer electrode 1516 does not cover second end 1509 of tube 1506 or extend to cap 1504.

In the preferred embodiment, when module 1500 is assembled, coupler 1512 and ion dispenser 1514 are positioned approximately 30-50% inside of tube 1506, although any suitable percentage is acceptable. In this manner, electrical current is delivered to the inside of, and approximately the center of, inner electrode 1518.

Ion dispenser 1514 is preferably connected to a second end 1507 of coupler 1512 and functions in the same manner, and is preferably formed of the same material, as ion dispenser 108.

Module 1500 is curved and to accommodate this curved shape, tube 1506, coupler 1512, inner electrode 1518 and outer electrode 1516 are suitably curved. Module 1500 includes a first end sleeve 1502, a second end sleeve 1504 and a curved body portion 1506. A connector 1508 is configured to connect to a power source (not shown). End sleeve 1502 (previously described) has a fastener 1510, which has the same structure and is utilized with the same components as fastener 113.

The coupler 1512, which functions in the same manner as coupler 106, is configured so it has a curve that approximates or is equal to the curve of tube 1506, so that coupler 1512 is approximately centered, or centered, in curved tube 1506.

Figure 24A:
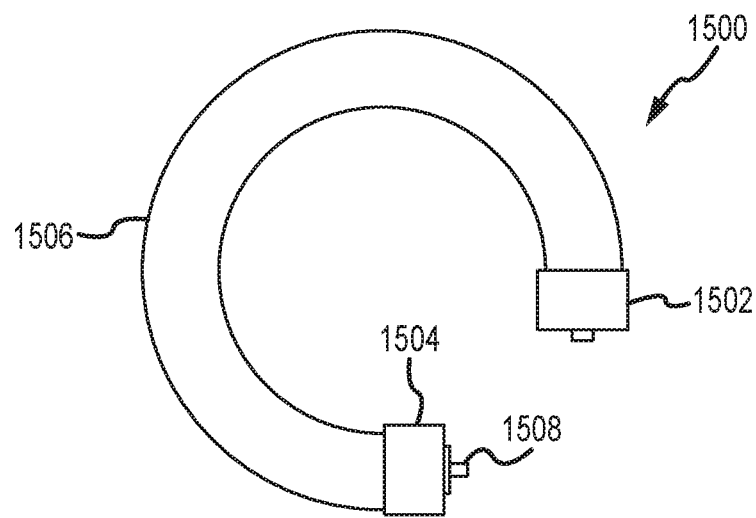
FIG. 24A is a top view of the tube shown in FIG. 24.
Figure 24B:
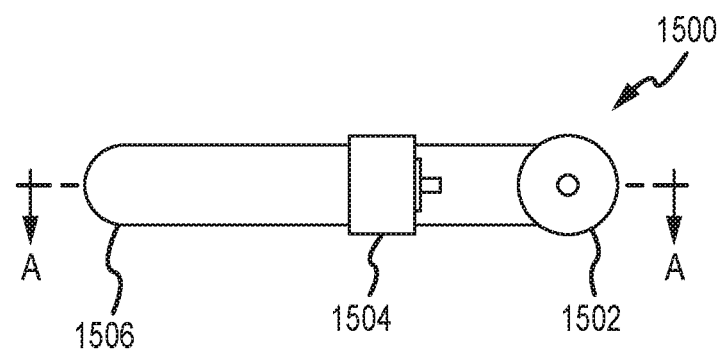
FIG. 24B is a side view of the tube shown in FIG. 24.
Figure 24C:
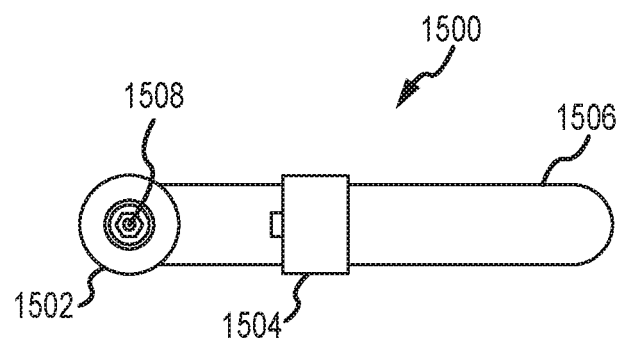
FIG. 24C is an alternative side view of the tube shown in FIG. 24.
Figure 24D:
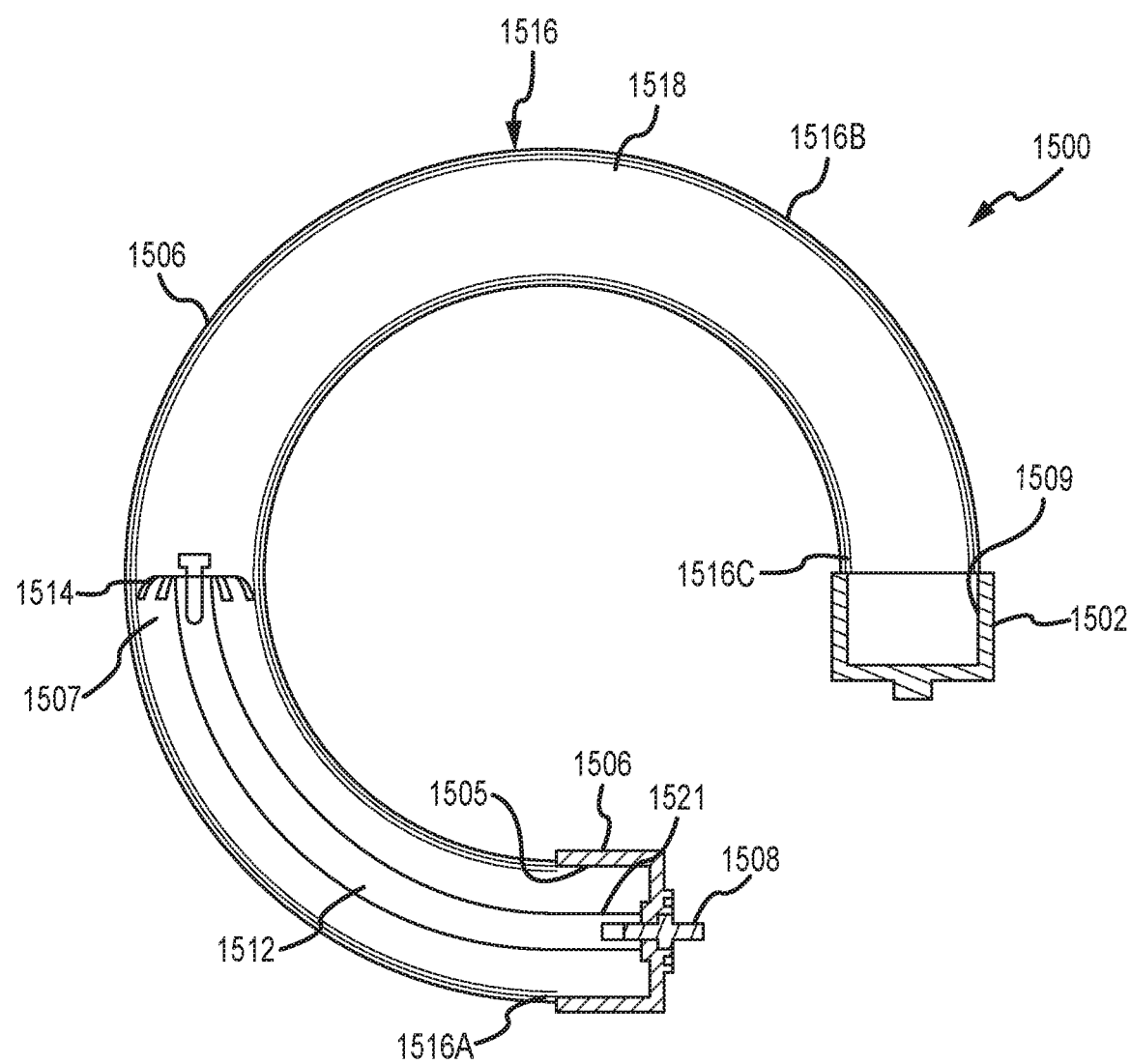
FIG. 24D is a cross-sectional view of the tube of FIG. 24B along line A-A.
Figure 24E:
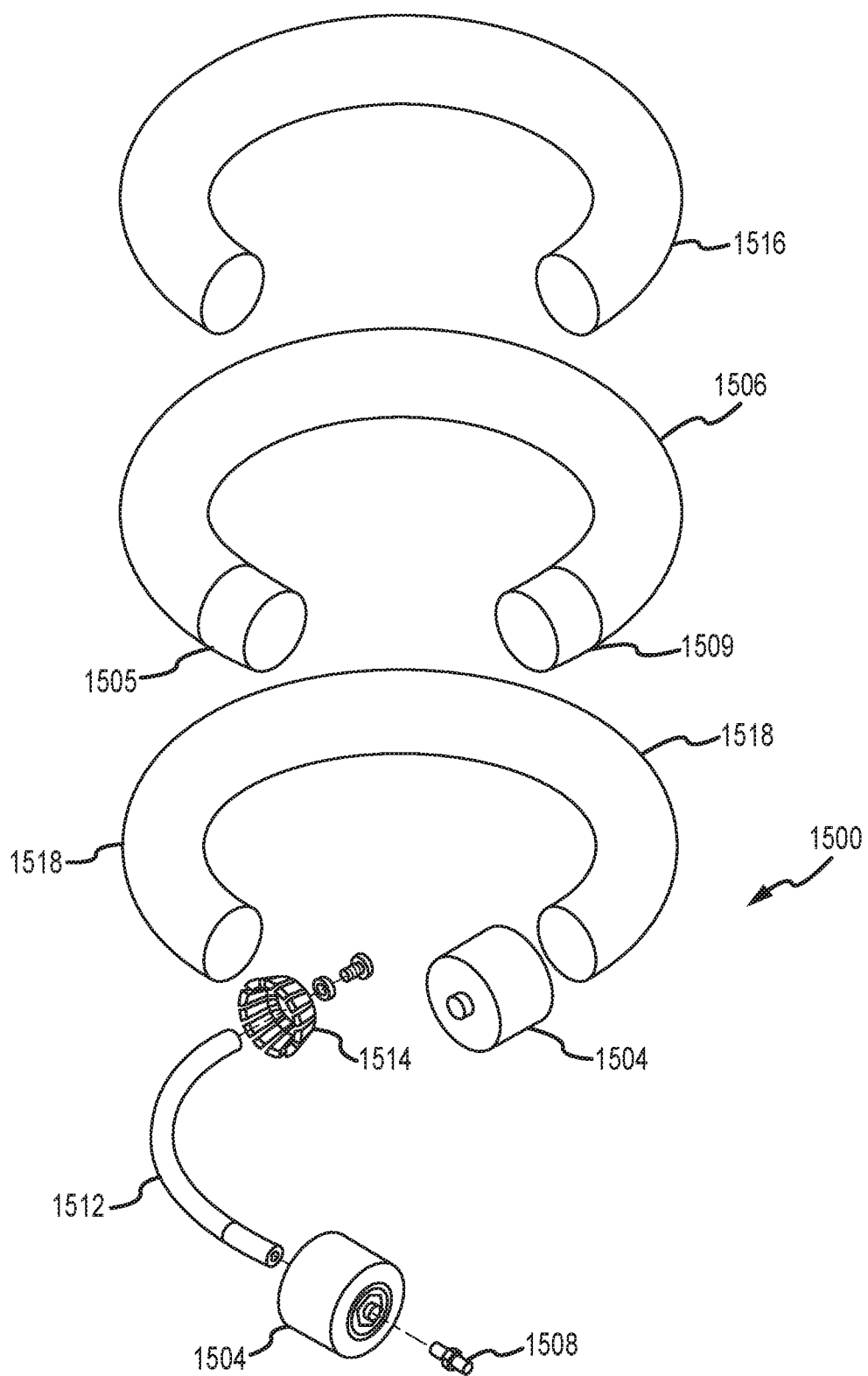
FIG. 24E is an exploded view of this tube shown in FIG. 24.
Figure 24F:
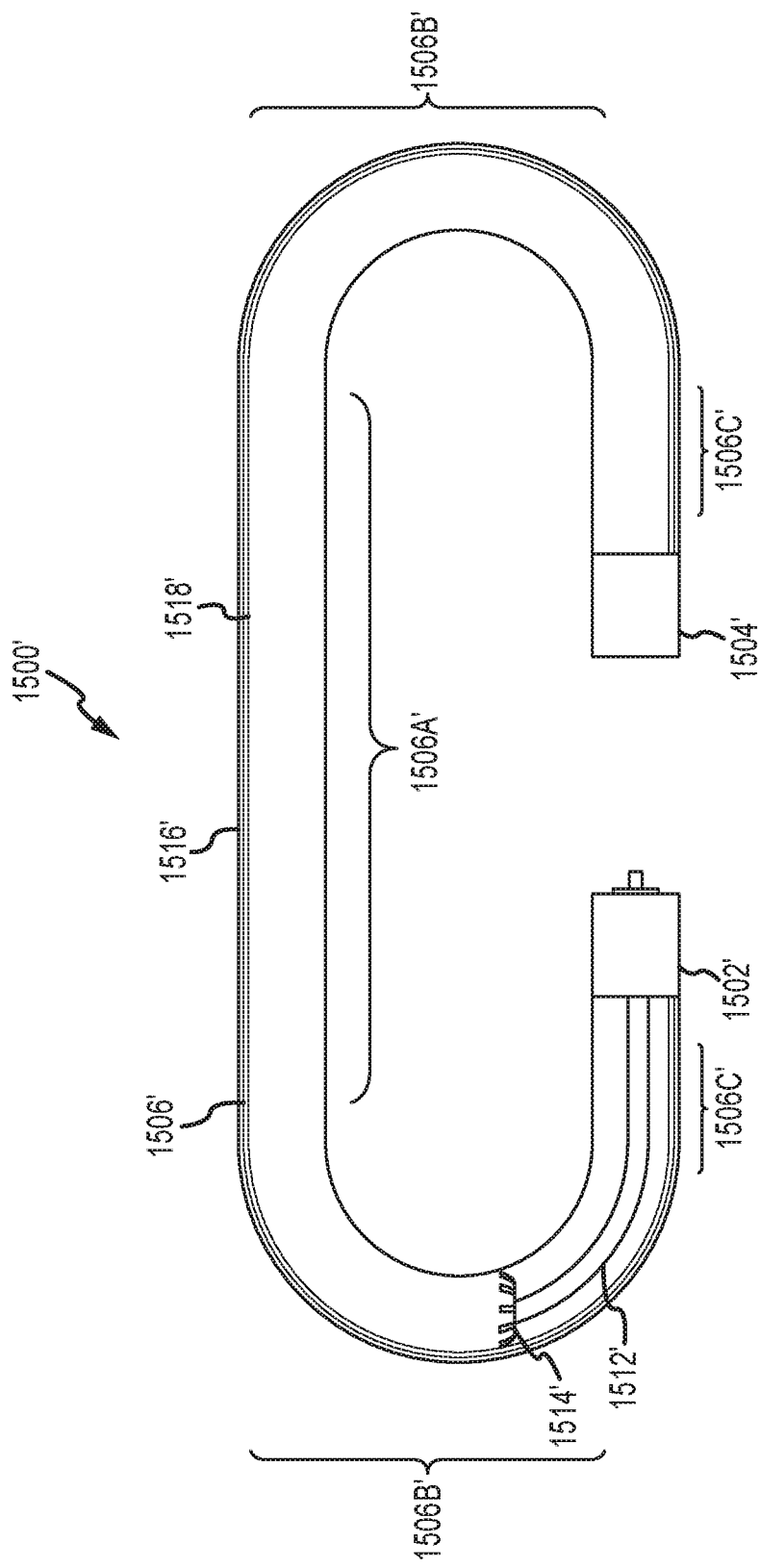
FIG. 24F is an alternate example of an ionization tube that may be used with aspects of the invention.

Ionization module 1500 may be in the shape of a continuous curve, or be straight along the central portion 1506A and have curves at side portions 1506B, as shown in FIG. 24F. Further, ends 1506C of tube 1506 may be straight or curved. If curved, end sleeves 1502 and 1504 are configured in a shape to fit on curved ends 1505 and 1509.

FIG. 24A shows a top view of ionization module 1500. FIG. 24B shows a side view of ionization module 1500. FIG. 24C is an alternate side view of ionization module 1500. FIG. 24D is a cross-sectional top view of module 1500 taken across line A-A of FIG. 24B. FIG. 24E is an exploded view of ionization module 1500. Not shown in FIGS. 24-24F is an ozone removal assembly, which is the same type of assembly as previously-described assembly 400 except that it would be shaped to fit at least partially over ionization module 1500 or 1500' and allow a space therebetween for air to pass through. Alternatively, as described below, the ozone dampening catalyst could be in a filter of any shape or size wherein the ionized air passes through the ozone dampening catalyst after it is ionized by the ionization module.

A tube 1500' with a straight section 1506A, curved side sections 1506B', and end sections 1506C' is shown in FIG. 24F. Coupler 1512' is configured to fit in tube 1506' so it is approximately centered or centered inside of tube 1506'. Ion dispenser 1514' is the same as ion dispenser 1514 shown in FIG. 24, which is the same as ion dispenser 108. End caps 1502', 1504' are configured to fit on straight end sections 1506C' of tube 1506'.

An advantage of making an ionization tube in one of these shapes is that tube 1500 or 1500' can have the same total area for ionization as for a straight tube, it can fit inside a smaller, or differently-sized, structure or space. Alternatively, it can provide a greater ionization area within the same space.

Figure 25A:
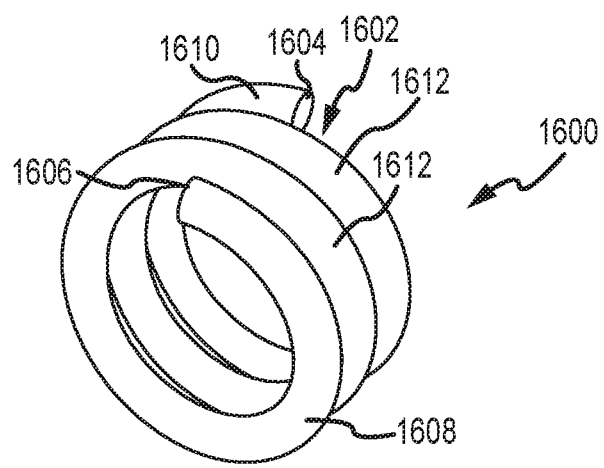
FIGS. 25A-25C show alternate helical tubes that may be used with aspects of the invention.

FIG. 25A shows a helical, multi-twist tube 1600 with a constant diameter. Tube 1600 has a body 1602 that includes an end 1604, an end 1606, two full coils 1612, and two partial coils 1608 and 1610. End caps (not shown), internal ionization structures (not shown), inner and outer electrodes (not shown), and an ozone removal assembly (not shown), are configured and sized to function with tube 1600 in the same preferred manner as described herein. As an example, the coupler and ion dispenser may be inserted through end 1604 or 1606, and may be positioned in up to 20%-60% of the length (as measured annularly) of tube 1600.

Figure 25B:
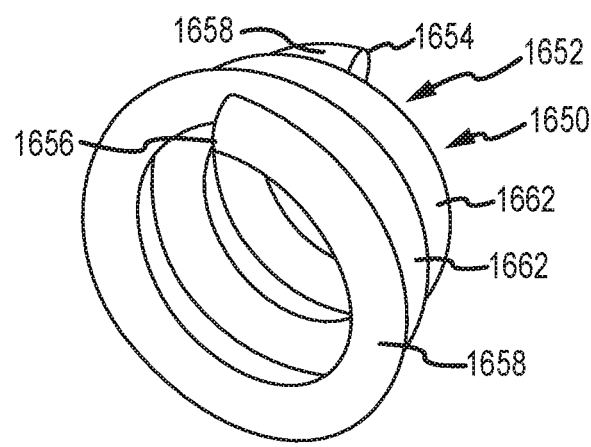

FIG. 25B shows a helical, multi-twist tube 1650 with a decreasing diameter moving from end 1656 to end 1654, which is also referred to herein as an inward helical shape. Tube 1650 has a body 1652 that includes an end 1654, an end 1656, two full coils 1662, and two partial coils 1658 and 1660. End caps (not shown), internal ionization structures (not shown), inner and outer electrodes (not shown), and an ozone removal assembly (not shown), are configured and sized to function with tube 1680 in the same manner as described herein, although these components would be configured to fit on or in tube 1650, or to otherwise function with tube 1650. As an example, the coupler and ion dispenser may be inserted through end 1654 or end 1656 and may be positioned in up to 20%-60% of the length (as measured annularly) of tube 1650.

Figure 25C:
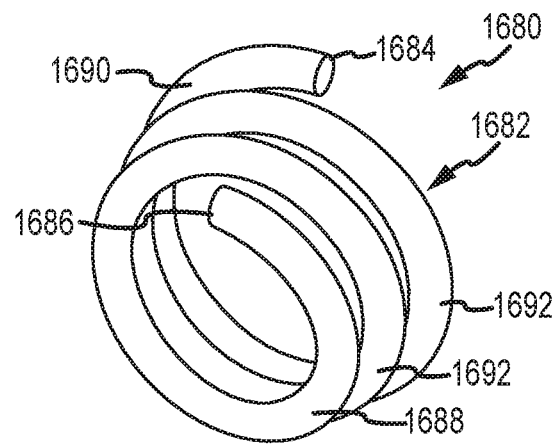

FIG. 25C shows a helical, multi-twist tube 1680 with an increasing diameter moving from end 1686 to 1684, which is also referred to herein as an outward helical shape. Tube 1680 has a body 1682 that includes an end 1684, an end 1686, two full coils 1692, and two partial coils 1688 and 1690. End caps (not shown), internal ionization structures (not shown), inner and outer electrodes (not shown), and an ozone removal assembly (not shown), are configured and sized to function with tube 1680 in the same manner as described herein, although these components are configured to fit on or in tube 1680, or to otherwise function with tube 1680.

Figure 26:
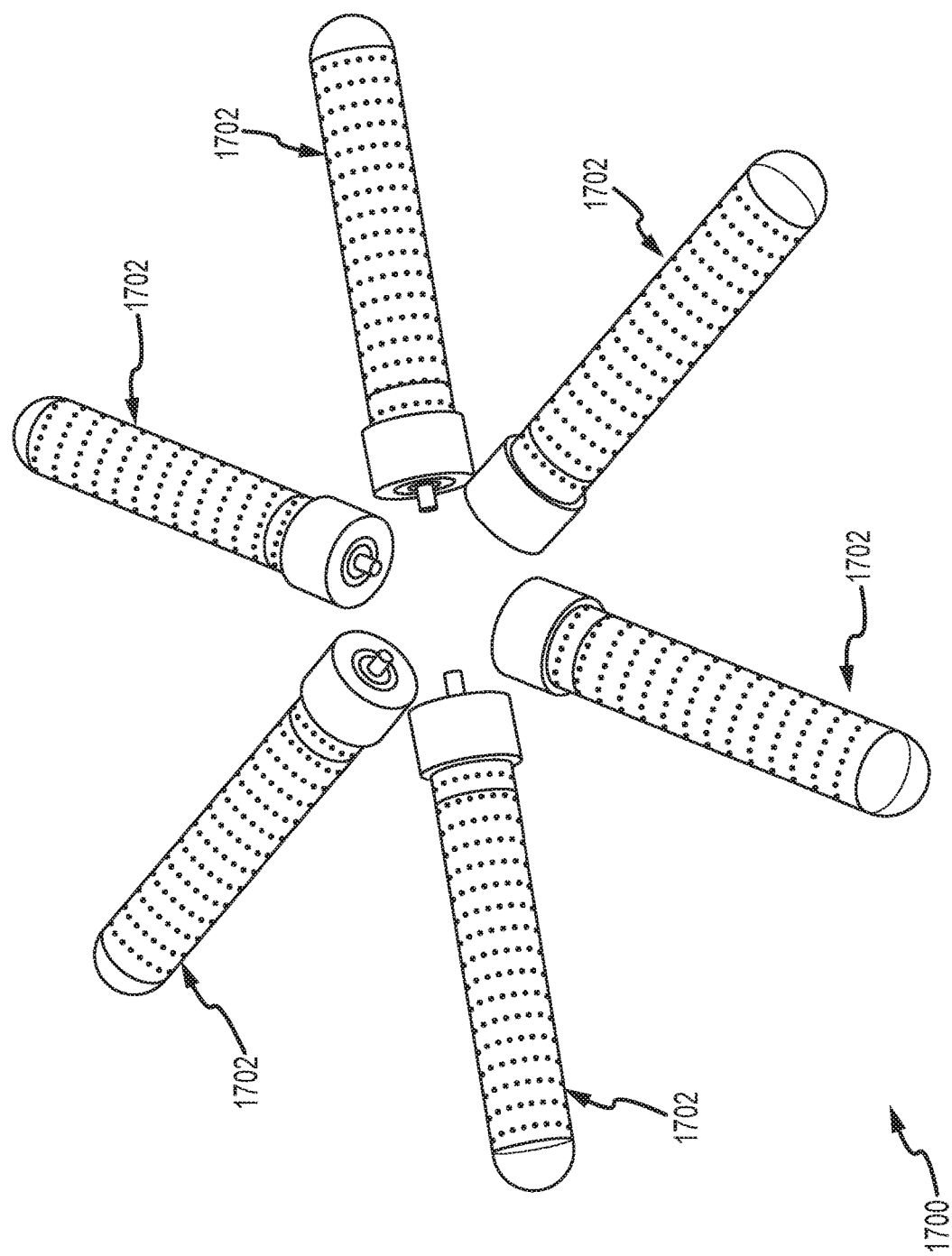
FIG. 26 shows an array of ionization tubes that may be used with aspects of the invention.

FIG. 26 shows a rotary configuration 1700 of multiple (or a plurality of) straight ionization modules 1702. Each module 1702 has any suitable structure, such as the preferred structure of previously-described module 110, with ion dispenser 108, inner electrode 114, coupler 106, outer electrode 112, cap 102, and ozone removal assembly 400. Although six tubes 702 are shown, any plurality of tubes, such as between three and eight tubes, can be arranged in a rotary configuration. An advantage of this configuration is that a greater overall tube surface area, and hence ionization area, is provided in a given space. In addition, each individual tube could have a length and/or diameter that is less than that of a standard ionization tube. For example, each tube may have a length of anywhere between 4" and 12"; or up to 4", 5", 6", 7", 8", 9", 10", 11", or 12"; or a length greater than 12". Each tube may also have an inner diameter of anywhere between ¼" to 1½"; or up to ¼", ½", ¾", 1", 1¼", 1½", 1¾", 2", 2¼", or 2½"; or greater than 2½".

Additionally, tubes used in configuration 1700 may have differing lengths and inner diameters.

Additionally, the ozone removal assemblies 400 on each tube 1702 could instead, or in addition to, be an ozone removal filter (such as filter 1780, described below), which could be below, above or beside tubes 1702, or that is otherwise downstream of the tubes 1702 according to the direction of the flow of air being ionized.

Supply Air Vent

Figure 27:
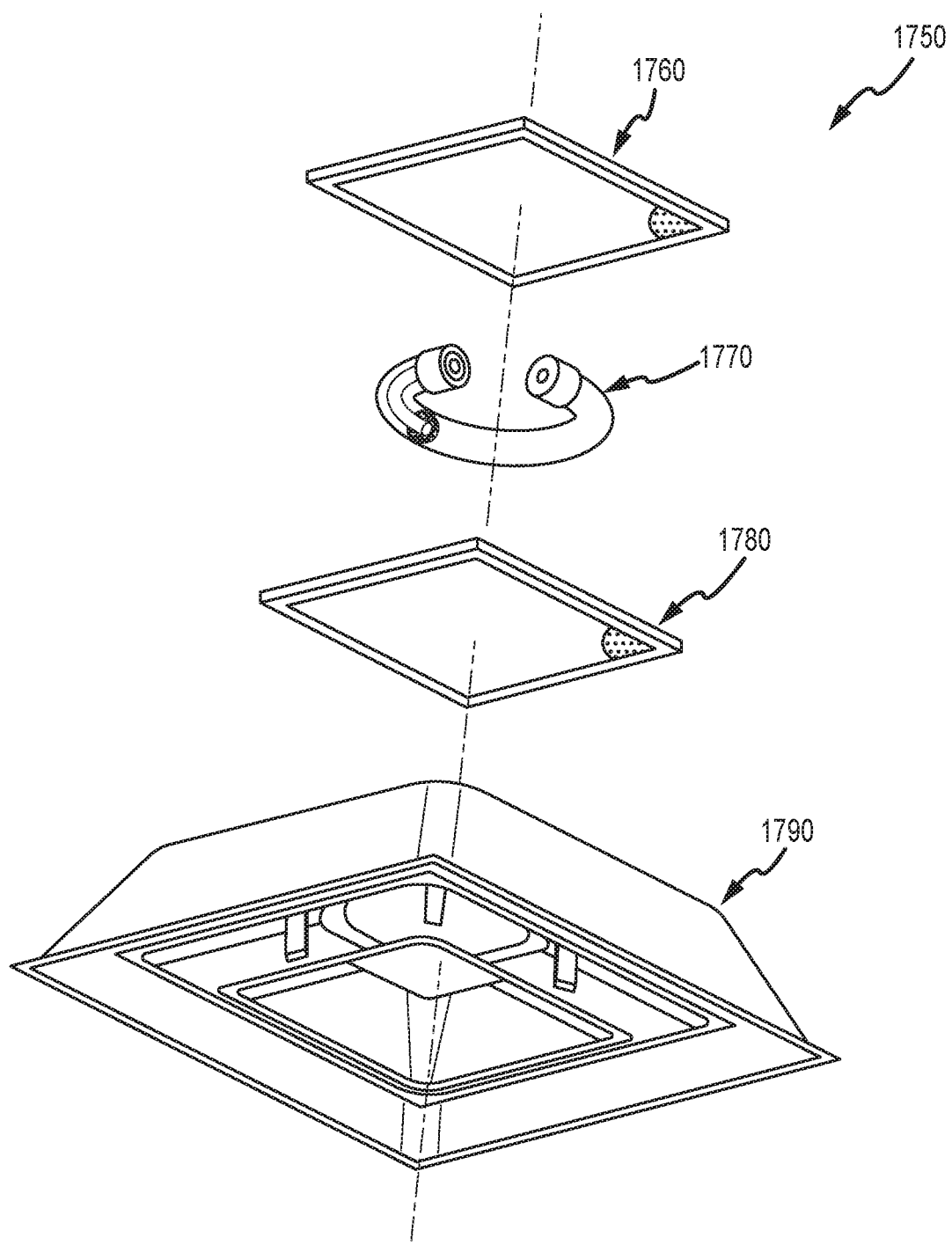
FIG. 27 shows an air supply vent utilizing an ionization system according to aspects of the invention.

FIG. 27 shows a supply air vent 1750 with an integral air ionization system. As shown, supply air vent 1750 has (1) a clean air filter 1760 (which is optional and need not be used); (2) an ionization module 1770, which as shown is a curved ionization unit, such as previously-described module 1500, but could be any suitable ionization module, such as module 1600, 1650, or 1680, or a single, straight module 110, or a plurality of straight modules 1702 in a rotary configuration as shown in FIG. 26, or a plurality of straight tubes placed side to side or in any suitable position; (3) an ozone removal filter 1780 beneath ionization unit 1770; and (4) vent frame 1790, which is configured to retain structures 1760, 1770, and 1780 and be mounted in an air supply vent. The ozone removal filter is shown as being flat, but it preferably has the same structure as defined for ozone removal assembly 400 and includes catalyst media 408, as previously described.

An optional fan (not shown) may be positioned between the clean air filter 1760 and ionization unit 1770, or above clean air filter 1760, or if there is no clear air filter 1760, above the ionization module 1770. If used, the fan is positioned and configured to push air past ionization unit 1770 and through ozone removal filter 1780, which is the normal flow of air through the air supply vent cover 1750 into a living or working space.

Airflow Sensors

Figure 28:
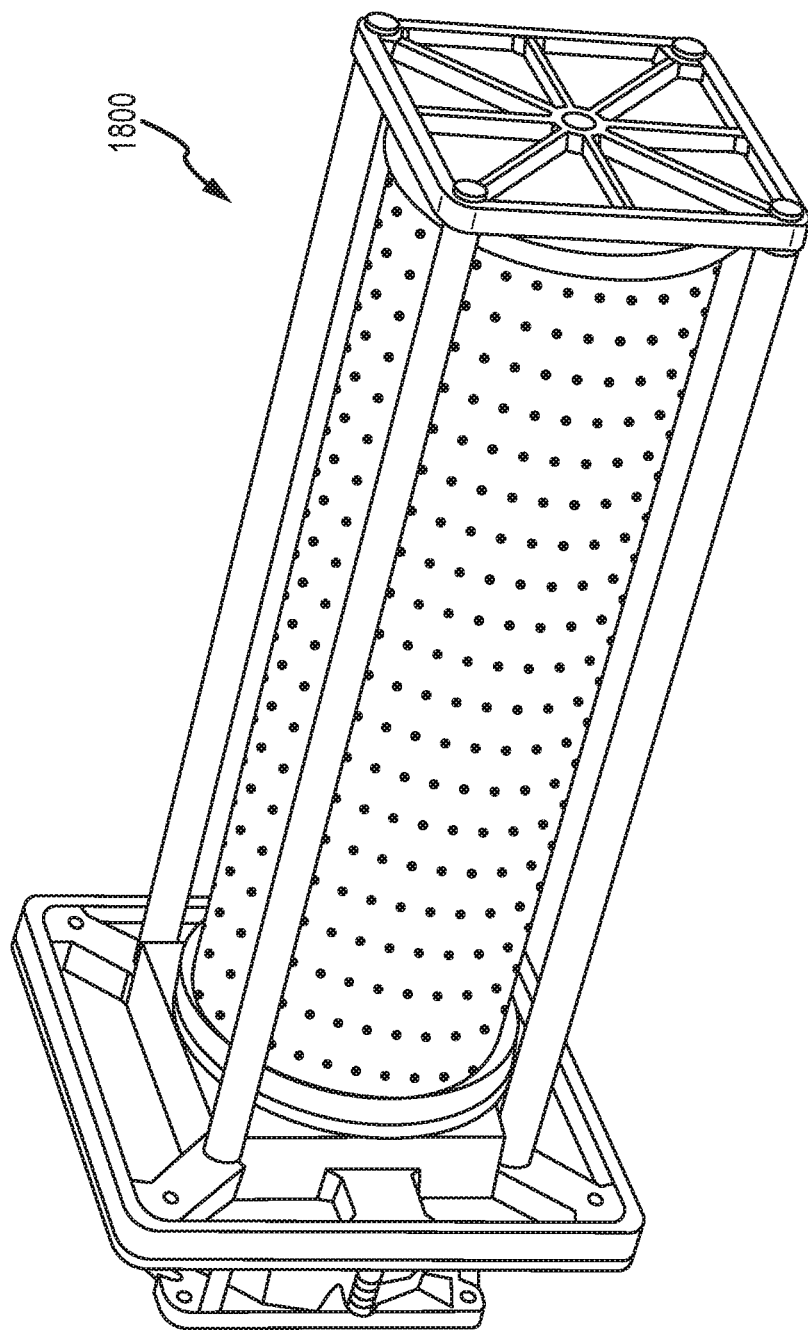
FIG. 28 shows an intelligent filter monitor system and device according to aspects of the invention.

FIG. 28 shows an ionization module 1800, which is the same as removable module 100 previously described. Module 1800, however, includes airflow sensors, which are known in the art, that detect the flow of air into the space between the ionization tube and the ozone filter. Based on the difference between the air flow rate at the time module 1800 is first installed and a current air flow rate, the air flow sensor can signal the controller and the controller can initiate an alert that the clean air filter (or preferably the entire ionization module 1800 should be changed). The alert could be noise, such as a "beep" recurring at set time intervals (such as any interval between five minutes and one hour. Or, the alert may be a continuous or flashing light signal or display of the control panel, such as lighted words that read "change filter," or "change ionization module." Accordingly, the controller must be programmed to include in it an air-flow rate that indicates replacement of an air filter, or assembly including and air filter, is required. This air-flow rate is determined by one or more of several factors for a given environment: (1) whether smokers are present and how much they smoke, (2) where the filter is located, such as in the kitchen (where there are many contaminants, or in a remote bedroom that's seldom used, (3) whether there are pets in the building and where the pets are located, (4) the number of occupants in the building, (5) activities in the building that would create particulates, and (6) the type of HVAC system used. In other words, instead of changing air filters based on a set period of time, the variables above would be entered into the controller and the controller would create an alert to change a filter when the air-flow rate is at a predetermined level that indicates the filter should be changed.

A filter such as filter 1760 or 1780 could also have associated air-flow sensors located at any suitable position (such as one or more at or near the center of the filter, plus additionally others on one or more sides and corners of the air filter) to detect when clean air filter 1760 or ozone removal filter 1780 should be changed. Such air-flow sensors, when they detect the air-flow through a filter is at too low a rate, could signal the controller, which could create an alert, preferably in one of the ways previously described.

Figure 29:
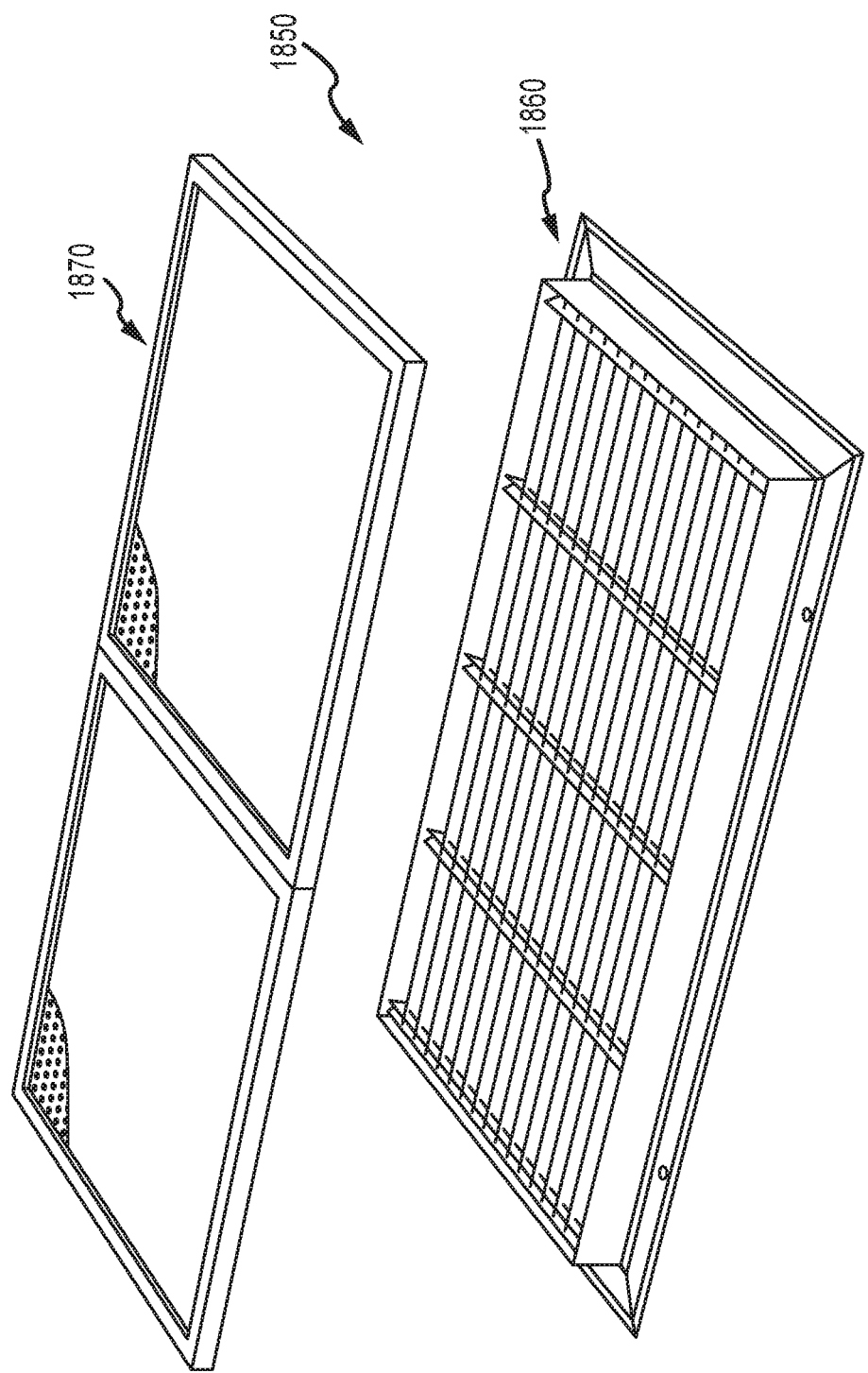
FIG. 29 shows a return air grill with a filter including an air flow sensor.

FIG. 29 shows a return air grill 1850 with a grill 1860 and one or more filters 1870. In the embodiment shown, the filters are monitored by air-flow sensors in one of the ways previously described.

Portable Unit

Figure 30:
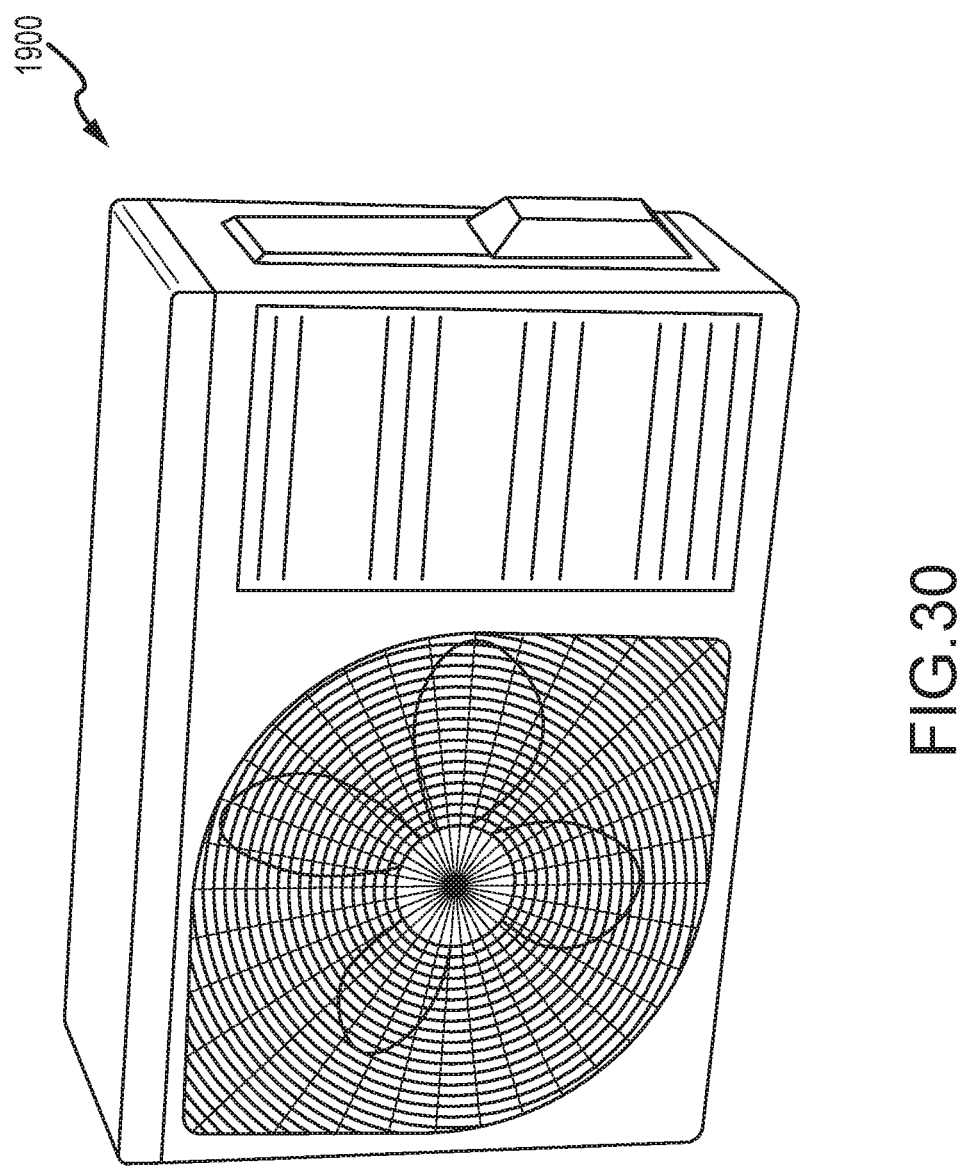
FIG. 30 shows a portable air ionization unit in accordance with aspects of the invention.

FIG. 30 shows a portable ionization unit 900 that utilizes ionization air cleaning according to the invention. Unit 1900 is portable and can be moved from room to room or building to building. It can be small enough to fit into a suitcase. Unit 1900 ionizes air in one of the manners previously described and otherwise functions in a manner previously described.

Alternate Ozone Removal Assembly Configurations

Any module, such as module 100, 1500, 1500', 1600, 1650, 1680, 1700, 1770, or 1800 could have any suitable clean air filter size or configuration (which are optional, but preferred) and also any suitable ozone removal assembly size or configuration, as long as the ionized air passes through the ozone removal assembly after being ionized. FIGS. 31-34 show various structures of ozone removal assemblies that may be utilized with one or more ionization module(s), it being understood that any suitable ozone removal assembly structure or ionization module may be utilized.

Figure 31A:
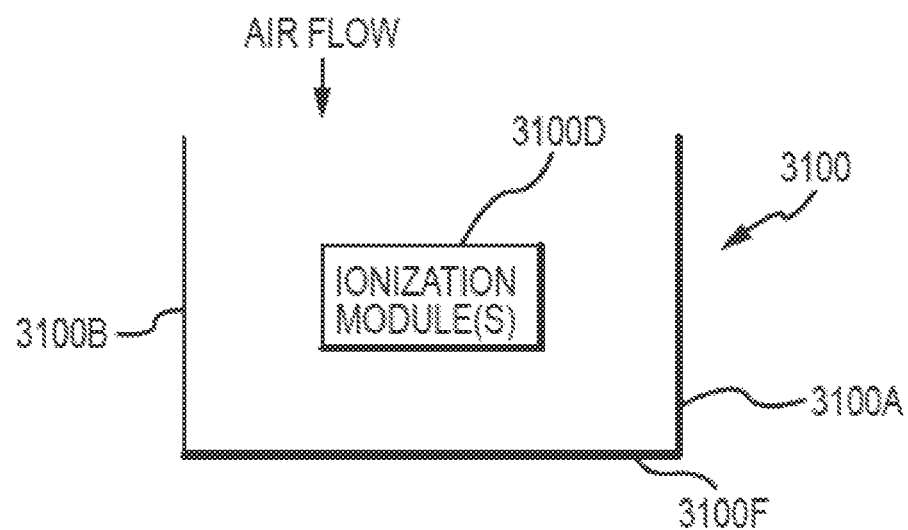
FIG. 31A shows a side view of an alternative ozone removal assembly.
Figure 31B:
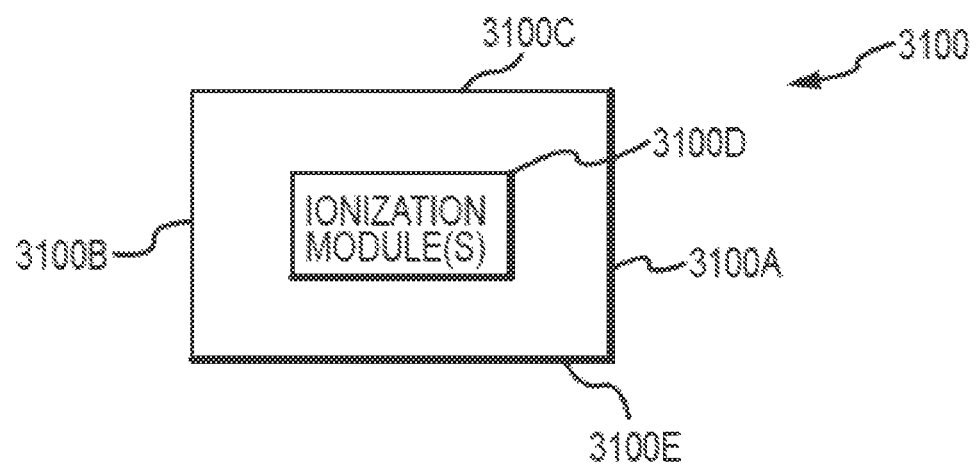
FIG. 31B shows a top view of the ozone removal assembly of FIG. 31A.

FIG. 31 shows an ozone removal assembly 3100 having a rectangular shape with an open top. Assembly 3100 has four sides 3100A, 3100B, 3100C, 3100E, a bottom 3100F, and an inner cavity 3100D. One or more ionization modules are preferably positioned in cavity 3100D. Air flows into cavity 3100D past the one or more ionization units and passes through bottom 3100F and/or sides 3100A, 3100B, 3100C and 3100E, one or more of which include ozone dampening catalyst to reduce ozone.

Figure 32A:
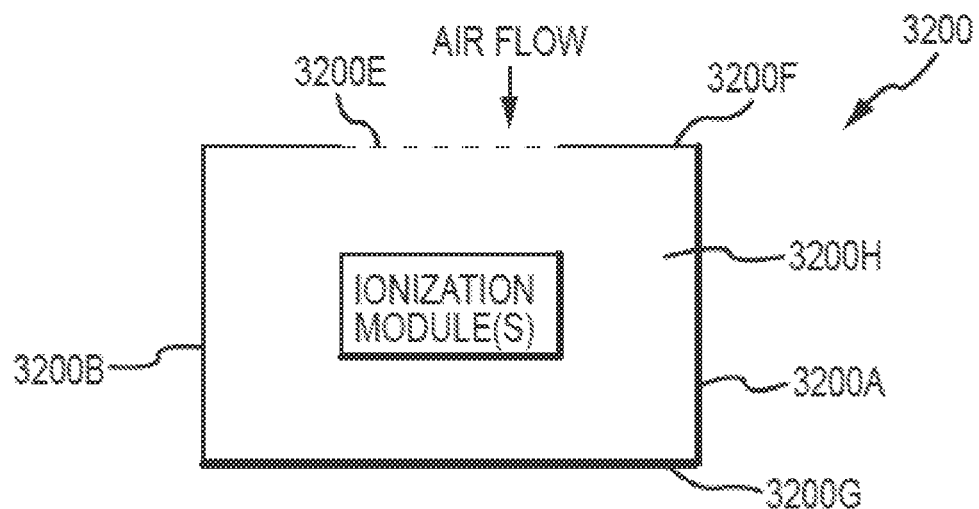
FIG. 32A shows a side view of an alternative ozone removal assembly.
Figure 32B:
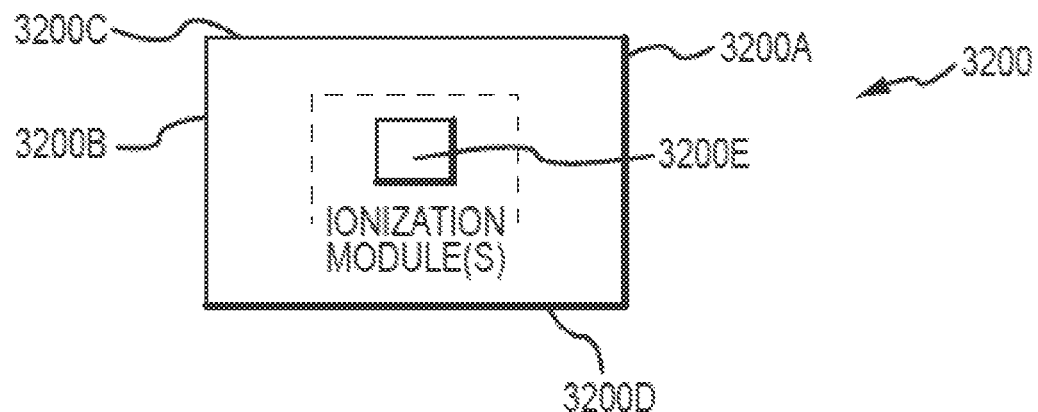
FIG. 32B shows a top view of the ozone removal assembly of FIG. 32A.

FIG. 32 shows an ozone removal assembly 3200 that is the same as assembly 3100 except that instead of having an open top, it has an opening 3200E in top surface 3200F through which air flows. Assembly 3200 has four sides 3200A, 3200B, 3200C, and 3200D. It also has a bottom 3200G, and a top 3200F having opening 3200E. A cavity 3200H preferably contains one or more ionization modules. Air flows into cavity 3200H through opening 3200E and is ionized. It then flows outward through one or more of walls 3200A, 3200B, 3200C, 3200D, 3200F, and 3200G, one or more of which includes ozone dampening catalyst.

Figure 33:
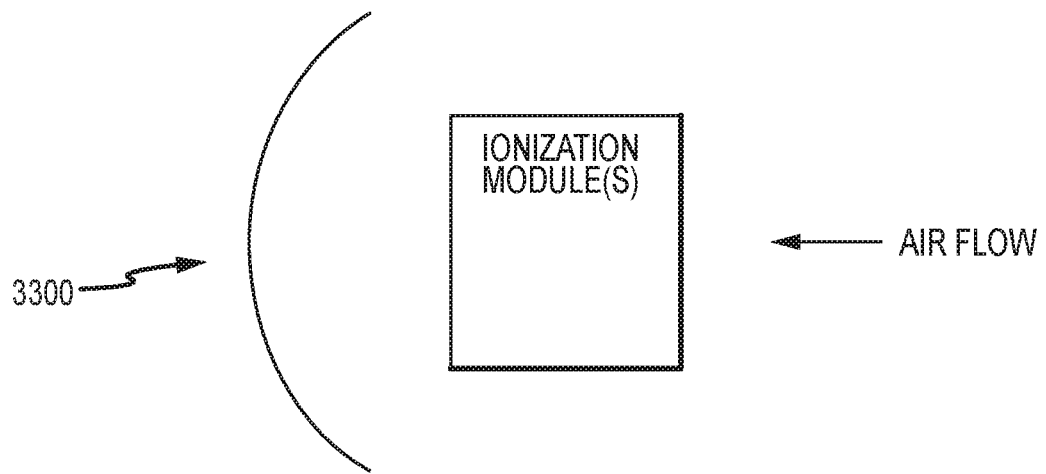
FIG. 33 shows a side view of an alternative ozone removal assembly.

FIG. 33 shows a curved ozone removal assembly 3300 on the side of one or more ionization modules. Air is flowed past the one or more ionization modules and then passes through ozone removal assembly 3300.

Figure 34:
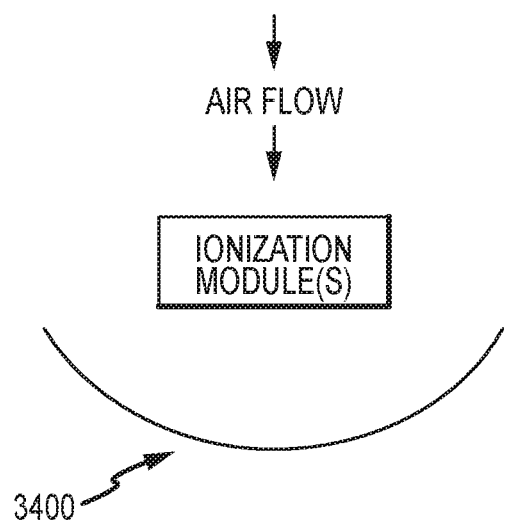
FIG. 34 shows a side view of an alternative ozone removal assembly.

FIG. 34 shows a curved ozone removal assembly 3400 beneath one or more ionization modules. Air is flowed past the one or more ionization modules and then passes through ozone removal assembly 3400.

As used herein, the terms "comprises," "comprising," or any other variation thereof, are intended to cover a non-exclusive inclusion, such that a process, method, article, or apparatus that comprises a list of limitations does not include only those elements but may include other limitations not expressly listed to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

Having thus described some embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed is:

1. An air ionization method comprising the steps of:
   (a) moving air into an enclosed space and into contact with one ion generator;
   (b) operating the one ion generator to generate ions into the air;
   (c) moving at least some of the air with ions outward sideways relative a longitudinal axis of the one ion generator and through a granulated ozone dampening catalyst for removing at least some ozone from the air, wherein the granulated ozone dampening catalyst is contained in an ozone removal assembly and the one ion generator is disposed at least partially within the ozone removal assembly, and
   (d) moving the at least some of the air out of the enclosed space.

2. The air ionization method of claim 1, wherein the one ion generator is configured to generate more negative ions than positive ions.

3. The air ionization method of claim 2, wherein the at least some of the air is negatively ionized.

4. The air ionization method of claim 1 that further includes the step of filtering the at least some the air before moving it into contact with the one ion generator.

5. The air ionization method of claim 4, wherein the step of filtering is performed by moving the at least some of the air through a filter that is positioned inside of the enclosed space.

6. The air ionization method of claim 5 that further comprises the step of measuring air flow through the air filter.

7. The air ionization method of claim 6 that further includes the step of determining when the air filter should be changed.

8. The air ionization method of claim 1 that further includes the step of moving the at least some of the air inside of the enclosed space towards the one ion generator.

9. The air ionization method of claim 8, wherein the step of moving the at least some of the air inside of the enclosed space is performed by operating a fan that is positioned inside of the enclosed space.

10. The air ionization method of claim 1 that further includes the step of measuring an ion amount in the air and operating the one ion generator to produce fewer or more ions based at least in part on the measured ion amount.

11. The air ionization method of claim 1 that further includes the step of measuring at least one of the following of the air: an ozone level, an air temperature, a particulate level, a carbon monoxide level, and a humidity.

12. The method of claim 11 that further includes the step of operating the one ion generator to produce fewer or more ions based at least in part on the measured amount in the air of at least one of: the ozone level, the air temperature, the particulate level, the carbon monoxide level, and the humidity.

13. The air ionization method of claim 1, wherein the step of moving the at least some of the air into contact with the one ion generator comprises moving air into a space between the one ion generator and an ozone removal assembly in which the granular ozone dampening catalyst is contained.

14. The air ionization method of claim 13, wherein responsive to operation of a fan, air is moved into the space between the one ion generator and the ozone removal assembly.

15. The air ionization method of claim 13, wherein the one ion generator and the ozone removal assembly are constructed as a single unit, and that further comprises the steps of (a) removing the single unit from a HVAC duct, and (b) replacing the single unit with another single unit.

16. The air ionization method of claim 15, wherein the single unit further includes a mounting frame mounted to the HVAC duct, and the step of removing comprises removing the mounting frame from the HVAC duct.

17. The air ionization method of claim 15, wherein the another single unit further includes a second mounting frame, and the step of replacing comprises mounting the second mounting frame to the HVAC duct.

18. The air ionization method of claim 1, wherein the at least some of the air is negatively ionized.

19. An air ionization method comprising the steps of:
   (a) moving air into an enclosed space, and between one or more ion generators and an ozone removal assembly in which a granular ozone removal catalyst is contained, and into contact with the one or more ion generators wherein the one or more ion generators are disposed at least partially within the ozone removal assembly;
   (b) operating the one or more ion generators to generate ions into the air in the space between the one or more ion generators and the ozone removal assembly;
   (c) moving at least some of the air with ions through the granulated ozone removal catalyst in order to remove at least some ozone from the air; and
   (d) moving the at least some of the air out of the enclosed space.

20. The air ionization method of claim 19, wherein the one or more ion generators are configured to generate more negative ions than positive ions.

21. The air ionization method of claim 19 that further includes the step of filtering the air before moving it into contact with the one or more ion generators.

22. The air ionization method of claim 21, wherein the step of filtering is performed by moving at least some of the air through a filter that is positioned inside of the enclosed space.

23. The air ionization method of claim 22 that further comprises the step of measuring air flow through the air filter.

24. The air ionization method of claim 23 that further includes the step of determining when the air filter should be changed.

25. The air ionization method of claim 19, wherein the step of moving the air is performed by operating a fan.

26. The air ionization method of claim 19, wherein the step of moving the at least some of the air is performed by operating a fan.

27. The air ionization method of claim 19 that further includes the step of measuring an ion amount in the air and operating the one or more ion generators to produce fewer or more ions based at least in part on the measured ion amount.

28. The air ionization method of claim 19 that further includes the step of measuring at least one of the following of the air: an ozone level, an air temperature, a particulate level, a carbon monoxide level, and a humidity.

29. The method of claim 28 that further includes the step of operating the one or more ion generators to produce fewer or more ions based at least in part on the measured amount in the air of at least one of: the ozone level, an air temperature, the particulate level, the carbon monoxide level, and the humidity.

30. The air ionization method of claim 19, wherein the step of moving the at least some of the air with ions into contact with the one or more ion generators comprises moving air into a space between the one or more ion generators and an ozone removal assembly in which the granular ozone dampening catalyst is contained.

31. The air ionization method of claim 30, wherein responsive to operation of a fan, air is moved into the space between the one or more ion generators and the ozone removal assembly.

32. The air ionization method of claim 19, wherein the one ion generator and ozone removal assembly are constructed as a single unit, and that further comprises the steps of (a) removing the single unit from a HVAC duct, and (b) replacing the single unit with another single unit.

33. The air ionization method of claim 32, wherein the single unit further includes a mounting frame mounted to the HVAC duct, and the step of removing comprises removing the mounting frame from the HVAC duct.

34. The air ionization method of claim 32, wherein the another single unit further includes a second mounting frame, and the step of replacing comprises mounting the second mounting frame to the HVAC duct.

* * * * *